(12) United States Patent
Ravinayagam et al.

(10) Patent No.: US 11,123,309 B2
(45) Date of Patent: Sep. 21, 2021

(54) METHODS FOR DRUG DELIVERY, TUMOR IMAGING, AND OXIDATIVE DEHYDROGENATION USING HIERARCHICAL ZSM-5 COMPLEX

(71) Applicant: Imam Abdulrahman Bin Faisal University, Dammam (SA)

(72) Inventors: Vijaya Ravinayagam, Dammam (SA); B. Rabindran Jermy, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 16/191,692

(22) Filed: Nov. 15, 2018

(65) Prior Publication Data
US 2020/0155480 A1 May 21, 2020

(51) Int. Cl.
| | | |
|---|---|---|
| *A61K 31/12* | (2006.01) | |
| *C08K 3/36* | (2006.01) | |
| *C01B 39/02* | (2006.01) | |
| *A61K 47/58* | (2017.01) | |
| *A61K 9/51* | (2006.01) | |
| *A61K 36/9066* | (2006.01) | |

(52) U.S. Cl.
CPC ............... *A61K 31/12* (2013.01); *A61K 9/51* (2013.01); *A61K 36/9066* (2013.01); *A61K 47/58* (2017.08); *C01B 39/02* (2013.01); *C08K 3/36* (2013.01)

(58) Field of Classification Search
CPC .......... A61K 31/12; A61K 47/58; A61K 9/51; A61K 36/9066; C08K 3/36; C01B 39/02
See application file for complete search history.

(56) References Cited

U.S. PATENT DOCUMENTS

| | | | |
|---|---|---|---|
| 2009/0060993 A1 | 3/2009 | Schwarz et al. | |
| 2010/0291387 A1* | 11/2010 | Chaumonnot | C01B 39/02 428/402 |
| 2012/0231079 A1* | 9/2012 | Gupta | A61K 31/366 424/486 |
| 2014/0010903 A1* | 1/2014 | Madhavamenon | A61K 31/12 424/756 |

FOREIGN PATENT DOCUMENTS

| | | |
|---|---|---|
| EP | 1 238 594 B1 | 9/2006 |
| WO | 2010/050897 A1 | 5/2010 |
| WO | 2017/221192 A1 | 12/2017 |
| WO | 2018/003974 A1 | 1/2018 |

OTHER PUBLICATIONS

Huang et al. (Journal of Materials Chemistry B (Year: 2016).*
Vergaro, et al. ; Halloysite Clay Nanotubes for Resveratrol Delivery to Cancer Cells ; Wiley Online Library ; Molecular Bioscience ; Aug. 8, 2012 ; Abstract ; 2 pages.
Popova, et al. ; Resveratrol loading on mesoporous silica and zeolite carriers by solid state method ; Bulgarian Chemical Communication vol. 46, Special Issue ; pp. 117-122 ; 2014 ; 7 Pages.
Moller, et al. ; Talented Mesoporous Silica Nanoparticles ; Chemistry of Materials 29, Issue 1 ; Nov. 1, 2016 ; Abstract I 1 page.
Peilin Huang et al., "Novel drug delivery nanosystems based on out-inside bifunctionalized mesoporous silica yolk-shell magnetic nanostars used as nanocarriers for curcumin", Journal of Materials Chemistry B, 2016, 4, pp. 46-56.

* cited by examiner

*Primary Examiner* — Snigdha Maewall
(74) *Attorney, Agent, or Firm* — Oblon, McClelland, Maier & Neustadt, L.L.P.

(57) ABSTRACT

The invention is directed to hierarchical aluminosilicates that contain both micro- and meso-pores, to methods for loading and delivering poorly soluble antioxidants such as CoQ10 and curcumin to subjects, and to a top-down method for producing hierarchical aluminosilicates.

8 Claims, 29 Drawing Sheets

METHODS FOR DRUG DELIVERY, TUMOR IMAGING, AND OXIDATIVE DEHYDROGENATION USING HIERARCHICAL ZSM-5 COMPLEX

BACKGROUND

Field of the Invention

This technology relates to the fields of silica materials science, nanomedicine and pharmacology.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Antioxidant adsorption on mesostructured silica is a topic of interest relevant to the pharmaceutical, food, and cosmetic industries; F. Arriagada, O. Correa, G. Gunther, S. Nonell, F. Mura, C. Olea-Azar, J. Morales, *Morin Flavonoid Adsorbed on Mesoporous Silica, a Novel Antioxidant Nanomaterial*, PLoS ONE 11 (2016) e0164507. Antioxidants are known to act against cancers such as leukemia, colon and lung cancer cells, and other metabolic disorders through their abilities to scavenge free radicals.

Coenzyme Q10 (CoQ10) is a natural fat-soluble, vitamin-like, ubiquitously existing benzoquinone derivative built with a quinone structure. The chemical structure of Coenzyme Q10 consists of 10 isoprene units, each having five carbons, forming a polyisoprene chain; J. C. Rodriguez-Aguilera, A. B. Cortes, D. J. M. Fernandez-Ayala, P. Navas, *Biochemical Assessment of Coenzyme Q10 Deficiency*, J. Clin. Med. 6 (2017) 27. It acts primarily as an antioxidant, a membrane stabilizer, and a cofactor in the production of adenosine triphosphate (ATP) in the process known as oxidative phosphorylation, a process which produces ATP needed for cellular biosynthesis. CoQ10 acts as a regenerating antioxidant and a high concentration of quinol, a reduced form of CoQ10, in cell membranes maintains proper antioxidation either by direct reaction with free radicals or by enhancing the regeneration of tocopherol and ascorbate which in turn eliminate radicals.

Factors such as genetic mutation, ageing, cancer and use of statin-type drugs can decrease levels of CoQ10 in peripheral blood and in tissues, but substantial decreases in CoQ10 levels cannot be adequately compensated by a normal diet. This makes dietary supplementation with CoQ10 desirable; U. Alehagen, P. Johansson, J. Aaseth, J. Alexander, D. Wagsater, *Significant changes in circulating microRNA by dietary supplementation of selenium and coenzyme Q10 in healthy elderly males. A subgroup analysis of a prospective randomized double-blind placebo-controlled trial among elderly Swedish citizens*, PLoS ONE 12 (2017) e0174880. Nevertheless, supplementation with CoQ10 faces a number of obstacles including that CoQ10 is not chemically stable, is light sensitive, has a high molecular weight, and has low bioavailability. These problems have impeded the development of a reliable delivery system for CoQ10; Y. Matsuda, R. Masahara, *Photostability of solid-state ubidecarenone at ordinary and elevated temperatures under exaggerated UV irradiation*. J Pharm Sci 72 (1983) 1198-1203; Q. Li, S. Yang, Y. Li, X. Xue, Y. Huang, H. Luo, Y. Zhang, Z. Lu. *Comparative Evaluation of Soluble and Insoluble-Bound Phenolics and Antioxidant Activity of Two Chinese Mistletoes*, Molecules, 23,359, (2018) https://doi:10.3390/molecules23020359.

Curcumin, like CoQ10, has poor bioavailability that limits its use as a physiological antioxidant. It is a compound built with a bulky, hydrophobic polyphenol structure that renders it substantially insoluble in physiological fluids and severely limits its bioavailability.

Vitamin C (L-ascorbic acid) is a water-soluble vitamin which cannot be synthesized or stored in human body and is thus obtained mainly from the diet. Vitamin C is an essential co-factor in maintaining enzymes involved in the synthesis of collagen, carnitine and neurotransmitters. Vitamin C is also necessary for maximal activity of some hormones, transformation of cholesterol to bile acids as well as for bioavailability and absorption of iron. In addition to its role as a potent antioxidant, Vitamin C has the capability to acts as a co-antioxidant in the regeneration of other antioxidants.

Antioxidants such as CoQ10, curcumin, and ascorbic acid scavenge free radicals and are medically useful if they can be delivered to a target site in sufficient concentrations. Such uses include promotion of tumor regression, enhancement of pulmonary functions, enhancement of detoxification such as use as antihepatoxic agents, enhancement of cellular bioenergetics and use in treatment of metabolic disorders; N. M. Zaki, *Strategies for oral delivery and mitochondrial targeting of CoQ10*, Drug Delivery, 23 (2016) 1868-1881.

Controlled drug delivery and therapeutic or diagnostic use of nanoparticles or other materials such as mesoporous silicas have been investigated by many groups. These methods might be used to help deliver antioxidants like CoQ10 or curcumin, however, existing methods or modes of drug delivery face a number of obstacles; K. Park, *Drug delivery of the future: Chasing the invisible gorilla*, J Control Release 240 (2016) 2-8; J. Guo, K. Rahme, Y. He, L-L. Li, J. D Holmes, C. M O'Driscoll, *Gold nanoparticles enlighten the future of cancer theranostics*, Int. J. Nanomed. 12 (2017) 6131-6152.

Mesoporous aluminosilicates, such as the meso-M41S family of molecular sieves, have textural characteristics that set them apart from conventional zeolites. A mesoporous material is a material containing pores with diameters between 2 and 50 nm according to IUPAC nomenclature, while a microporous material contains pores with diameters less than 2 nm. The meso-M41S family of sieves has been studied for use in the fields of petroleum refining, polymer, and petrochemical manufacture and as catalysts for reactions including aromatic dealkylation, cracking, and hydrocracking.

The meso M41S family has been synthesized using a hydrothermal technique in a basic medium in the presence of quaternary trimethylammonium cations ($C_{16}$TMABr, CTAB). The resulting materials possess a large surface area (~1500 $m^2$/g), designable pore sizes (1.5-10 nm), and ordered nanochannels; J. S. Beck, C. Vartuli, W. J. Roth, M. E. Leonowicz, C. T. Kresge, K. D. Schmitt, C. T-W. Chu, D. H. Olson, E. W. Sheppard, S. B. McCullen, J. B. Higgins, J. L. Schlenker, J. Am. Chem. Soc. 114 (1992) 10834.

Mesoporous silicas, such as MCM-41, MCM-48, and SBA-15 have been reported to be effective nanocarriers for several types of antioxidants and proteins; A. Vinu, N. Gokulakrishnan, V. V. Balasubramanian, S. Alam, M. P. Kapoor, K. Ariga, T. Mori. *Three-Dimensional Ultralarge-Pore Ia3d Mesoporous Silica with Various Pore Diameters and Their Application in Biomolecule Immobilization*, Chem. Eur. J. 14 (2008) 11529-11538; G. Chandrasekar, A.

Vinu, V. Murugesan, M. Hartmann, *Adsorption of vitamin E on mesoporous silica molecular sieves*, Studies in Surface Science and Catalysis, 158(B), (2005) 1169-1176; L. Ji, A. Katiyar, N. G. Pinto, M. Jaroniec, and P. G. Smirniotis, *Al-MCM*-41 *sorbents for bovine serum albumin: relation between Al content and performance*, Micropor. Mesopor. Mater, 75 (2004) 221-229; Y. Yokogawa, T. Toma, A. Saito, A. Nakamura, I. Kishida, *Biomolecules Loading and Mesoporous SBA*-15 *Pore Sizes*, Bioceramics Development and Applications, 1 (2011) 1-3.

MCM-41 (Mobil Composition of Matter No. 41) is a mesoporous silica material with a hierarchical structure from a family of silicate and alumosilicate solids that were developed by researchers at Mobil Oil Corporation and that can be used as catalysts or catalyst supports. MCM-41 and MCM-48 both comprise an amorphous silica wall and possess long range ordered framework with uniform mesopores. These materials also possess large surface area, which can be up to more than 1,000 $m^2g^{-1}$. The pore diameter of these materials can be controlled to fall within a mesoporous range between 1.5 and 20 nm by adjusting the synthesis conditions and/or by employing surfactants with different chain lengths in their preparation.

SBA-15 is a mesoporous silica having a <150 µm particle size, pore size 8 nm, and hexagonal pore morphology; it has been loaded with poorly water-soluble compounds; Van Speybroeck, Michiel; Barillaro, Valery; Thi, Thao Do; Mellaerts, Randy; Martens, Johan; Van Humbeeck, Jan; Vermant, Jan; Annaert, Pieter; et al. (2009). *Ordered mesoporous silica material SBA*-15: *A broad-spectrum formulation platform for poorly soluble drugs*. Journal of Pharmaceutical Sciences. 98 (8): 2648-58 incorporated herein by reference.

The inventors previously studied the use of shaped mesoporous silica in conjunction with a phenolic acidic type antioxidant gallic acid; Vijaya Ravinayagam and B. Rabindran Jermy, *Studying the loading effect of acidic type antioxidant on amorphous silica nanoparticle carriers*, Journal of Nanoparticle Research, 19 (2017) 190 incorporated herein by reference. They also studied a hierarchical mesosilicalite/Si-MCM-41 in combination with cisplatin for anticancer activity; B Rabindran Jermy, Sadananda Acharya, Vijaya Ravinayagam, Hajer Saleh Alghamdi, Sultan Akhtar, Rehab S Basuwaidan, *Hierarchical mesosilicalite nanoformulation integrated with cisplatin exhibits target-specific efficient anticancer activity*, Appl Nanosci. 2018. https:// https://_doi.org/10.1007/s13204-018-0786-9 incorporated herein by reference. The inventors sought to provide an aluminosilicate with new properties that would retain or expand the useful chemical, thermal and hydrothermal stabilities of such compounds to enhance loading and delivery of a payload molecule such as an antioxidant Zeolites are microporous, aluminosilicate minerals commonly used as commercial adsorbents and catalysts. ZSM-5 or Zeolite Socony Mobil-5, (framework type WI from ZSM-5 (five)) is an aluminosilicate zeolite belonging to the pentasil family of zeolites. Its chemical formula is $Na_n Al_n Si_{96-n} O_{192} \cdot 16H_2O$ (0<n<27). ZSM-5 is widely used in the petroleum industry as a heterogeneous catalyst for hydrocarbon isomerization reactions. Microporous zeolites are well known inorganic molecular sieves extensively used to adsorb heavy metal ions and in catalysts. Micromesoporous M-ZSM-5 composites have been hydrothermally synthesized by the self-assembly of precursors, alkali-treated ZSM-5 nanoparticles, with CTMABr surfactant in alkaline media and characterized by X-ray diffraction (XRD), $N_2$ adsorption, Fourier transform infrared (FT-IR) and transmission electron microscopy (TEM; C-M. Song, Z-F. Van, *Synthesis and characterization of M-ZSM*-5 *composites prepared from ZSM*-5 *zeolite*, Asia-Pac. J. Chem. Eng. 3 (2008) 275-283 incorporated herein by reference. However, structurally stable microporous or micro-mesoporous materials are not well explored for pharmaceutical or biomedical applications.

Various techniques have been proposed to improve accessibility of micropore active sites in zeolites like ZSM-5. These included preparation of zeolite nanoparticles, synthesis of mesozeolites using zeolite seed solution, steam assisted creation of mesopores, and chemical etching and use organic and carbon templates. For example, in the field of petrochemistry, mesoporous zeolites were modified through top-down methodology to promote petrochemical reactions (Y. Liu, W. Z. Zhang, T. J. Pinnavaia, Angew. Chem.-Int. Ed. 40, 1255, (2001) incorporated herein by reference) and for catalysis a combination of microporous ZSM-5 and mesoporous MCM-41 was found to promote toluene alkylation and catalytic cracking; W. Alabi, L. Atanda, B. Rabindran Jermy, S. Al-Khattaf, *Kinetics of toluene alkylation with methanol catalyzed by pure and hybridized HZSM*-5 *catalysts*, Chemical Engineering Journal, 195-196 (2012) 276-288; T. Odedairo, R. J. Balasamy and S. Al-Khattaf, *Aromatic transformation over ZSM*-5/ *MCM*-41 *composites with adjustable porosity in fluidized bed reactor*, Catal. Sci. Technol. 2 (2012) 1275-1286 incorporated herein by reference.

It has not been previously proposed to employ hierarchical zeolites to load and deliver bulky molecular sized antioxidants such as CoQ10 or curcumin.

In view of the low bioavailability of these antioxidants, the inventors sought to develop a nanocarrier that would increase antioxidant bioavailability, for example, by providing a poorly soluble antioxidant in a noncrystalline, amorphous state that is more bioavailable or in a form suitable for targeted antioxidant delivery or diagnosis, for example, for tumor diagnosis or biosensor applications. Consequently, the inventors studied the antioxidant adsorptive capacity of hierarchical ZSM-5 produced using ZSM-5 having different crystal sizes and different $SiO_2/Al_2O_3$ ratios; M. W. Munthali, M. A. Elsheikh, E. Johan, N. Matsue, *Proton Adsorption Selectivity of Zeolites in Aqueous Media: Effect of Si/Al Ratio of Zeolites*, Molecules 19 (2014) 20468-20481 incorporated herein by reference.

In one aspect of the present disclosure a series of meso-microporous aluminosilicates was obtained using certain structural and compositional parameters for loading, targeting and physiological release of antioxidants like CoQ10 and curcumin. Among the characteristics of meso-microporous aluminosilicates investigated were compositional characteristics (e.g., silica to alumina ratio 22-1,500), of different crystal sizes (0.5 µm, 2.0 µm and 3.0 µm), Si—O—Al ordering in the main framework, distribution of aluminum species In case of hierarchical ZSM-5-80 (0.62), the signal corresponding to the tetrahedral Al species decreases significantly and coexisting of four and six coordinated extra framework aluminum species are observed with alkaline treatment of top-down methodology, accessibility of pores or cages of variable sizes, hydration of active sites, nature of extra framework cations, as well as potentially limiting factors on antioxidant loading such as external surface area and presence, or shape or frequency of, micropores. In the case of ZSM-5-80 (0.62) sample, acid-base type interactions may be dominant. In particular, coordination of carbonyl group of quinone to the protonic site of zeolite and the electron rich double bond of isoprene unit to extra framework $Al^{3+}$ cation may form a coordination site at the accessible external surface area of hierarchical ZSM-5-80 (0.62).

BRIEF SUMMARY OF THE INVENTION

The present disclosure pertains to a ZSM-5-based hierarchical aluminosilicate that facilitates adsorption, delivery and release of poorly soluble antioxidants such as CoQ10 and curcumin that is produced by design of the surface features of the aluminosilicate such as micro- and meso pore sizes, surface area, pore volumes and/or acidic characteristics. In some embodiments, CoQ10 or curcumin are loaded onto a hierarchical aluminosilicate that has a $SiO_2/Al_2O_3$ ratio of about 60 to 100, preferably about 80, an external surface area of at least about 600 $m^2/g$, a pore volume ranging from about 0.5 to about 0.8 cc/g, and will contain 15-75% weak acid sites based on a total number of acidic sites, preferably about 40-50% weak acid sites. Such a hierarchical aluminosilicate-antioxidant composition may contain at least about 25 wt. % of the at least one antioxidant based on the total weight of the composition and may contain the antioxidant in a more bioavailable amorphous form as opposed to a less soluble crystalline form.

Methods for therapeutic delivery of an antioxidant to a subject in need thereof, such as someone suffering from a disease, disorder or condition characterized by abnormal levels of free radicals are also disclosed.

A method for producing ZSM-5-based hierarchical aluminosilicates by top-down surface modification of ZSM-5 with NaOH/CTAB is also disclosed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
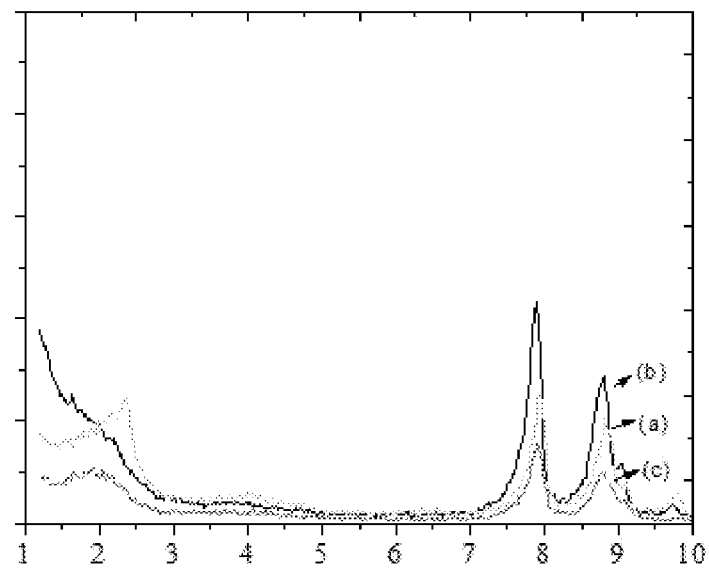
FIG. 1A. XRD spectra of hierarchical ZSM-5 ($SiO_2/Al_2O_3$=22-27) with different crystal sizes: 2.0 μm (a), 0.5 μm (b) and 3.0 μm (c) that were alkaline treated.

CoQ10 conforms to the following chemical structure:

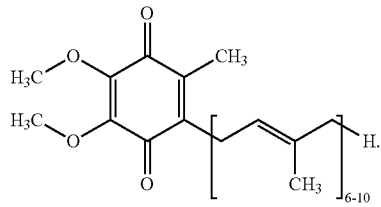

CoQ10 is a 1,4-benzoquinone, where Q refers to the quinone chemical group and 10 refers to the number of isoprenyl chemical subunits in its tail. Other forms of Coenzyme Q may be distinguished from CoQ10 by their number of isoprenyl subunits. In some embodiments of the invention CoQ10 or another CoQ may be included as a payload molecule in a hierarchical silica of the invention. A CoQ such as CoQ10 may be present in a crystalline or amorphous form or in a mixture of both crystalline and amorphous forms, for example at a ratio of 1-99 wt. %: 99-1 wt. %, 10-90 wt. %: 90-10 wt. %; 20-80 wt. %: 80-20 wt. %, 30-70 wt. %: 70-30 wt. %, 40-60 wt. %: 60-40 wt. % or about 50 wt. %: about 50 wt. % (or any intermediate ratio of crystalline:amorphous forms). Biocompatibility of hierarchical aluminosilicate which may be loaded with an antioxidant can be increased by encapsulation with chitosan, or poly (D,L-lactide-co-glycolide), or polyethylene glycol.

Curcumin has the following structure:

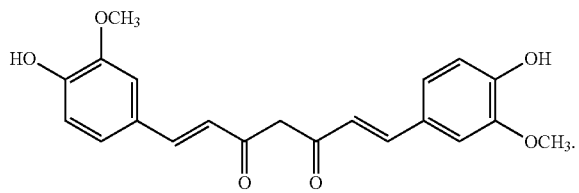 [SMILES: COc1cc(/C=C/C(=O)CC(=O)/C=C/c2ccc(O)c(OC)c2)ccc1O]

A curcuminoid is a linear diarylheptanoid. This class of compounds includes curcumin in both its keto and enolate forms as well as curcumin derivatives such as demethoxycurcumin and bisdemethoxycurcumin and their geometrical isomers and metabolites including sulfate conjugates and glucoronides. Other examples of curcumin derivatives or analogs include those described by Raja, et al., U.S. Pat. No. 9,447,023 B2, Raja, et al., U.S. Pat. No. 9,650,404 B2, Johnson, et al., U.S. Pat. No. 9,556,105 B2 or Vander Jagt, et al., U.S. Pat. No. 9,187,397 B2 (all incorporated by reference); especially for their descriptions of curcuminoid formulas and various chemical species of curcuminoids. In some embodiments of the invention curcumin or another curcuminoid may be included as a payload molecule in a hierarchical aluminosilicate of the invention.

Mixtures of curcuminoids are also contemplated such as one isolated from rhizomes of turmeric comprised of Curcumin (75-81%), Demethoxycurcumin (15-19%) and Bisdemethoxycurcumin (2.5-6.5%). The content of any one of a curcuminoid in a mixture may range from about 0 to about 100 wt. %, for example, 10-90 wt. %, 20-80 wt. %, 30-70 wt. %, 40-60 wt %., 50 wt. %, 40 wt. %, 33.3 wt. %, 30 wt. %, 20 wt. %, 10 wt. % or 5 wt % or 1 wt. %. A mixture may contain two, three or more different curcuminoids.

Curcumin may be present in a crystalline or amorphous form or in a mixture of both crystalline and amorphous forms, for example at a ratio of 1-99 wt. %:99-1 wt. %, 10-90 wt. %: 90-10 wt. %; 20-80 wt. %: 80-20 wt. %, 30-70 wt. %: 70-30 wt. %, 40-60 wt. %: 60-40 wt. % or about 50 wt. %: about 50 wt. % (or any intermediate ratio of crystalline:amorphous forms). In some embodiments disclosed herein, curcumin will be in an amorphous form to increase its solubility.

Curcumin and its derivatives are known for their antimicrobial, anti-oxidative, anti-inflammatory, and anti-cancer properties such as malignancies in the brain or nervous system. Curcumin has also been proposed as an agent to treat oxidative stress, such as oxidative stress in the brain, and for treatment of neurodegenerative disease like Alzheimer's disease ("AD") or Parkinson's disease ("PD"); Lee, et al., Curr. Neuropharmacol. 2013 July; 11(4): 338-378 (incorporated by reference).

Curcumin may also be functionalized or prepared as a conjugate with another moiety to modify or improve its pharmacokinetic properties. For example, curcumin can be adsorbed through functionalization to a silane, carboxylic acid, or biotin. Biocompatibility of a curcuminoid/hierarchical aluminosilicate can be increased by the modification with chitosan, or poly (D,L-lactide-co-glycolide), or polyethylene glycol.

Ascorbic Acid (Vitamin C). Increased intake of vitamin C may reverse oxidative effects of smoking, living in a polluted environment, obesity, over-eating, ingestion of oxidized foods (e.g., oxidized cholesterol), overexertion, cardiovascular disease, stroke, cancer, cancer treatment (e.g., drug treatment or radiation treatment), exposure to high levels of oxygen, recovery from inflammation or inflammatory effects of disease or disease treatment, malnutrition, as well as support proper functioning of the immune system and other physiological functions. Vitamin C may be formulated in a fat-soluble form, such as an ascorbyl palmitate, which after ingestion can be broken down into ascorbic acid and palmitic acid. Other forms include ascorbyl stearate and mineral ascorbates, such as sodium, potassium, calcium or magnesium ascorbate and may be generically described herein as "ascorbates". In some embodiments of the invention ascorbic acid, a fat-soluble ascorbate-type compound or a mineral ascorbate may be included as a payload molecule in a hierarchical aluminosilica of the invention. In some embodiments, an ascorbate may be loaded onto hexagonal MCM-41, cubic shaped mesostructure ULPFDU-12, micronsized spherical silica, AIMSU-F, SiKIT-6 or SiSBA-16 which were found to exhibit high a capacity for ascorbic acid loading, and admixed with a hierarchical aluminosilicate such as ZSM-5-80 (0.62), loaded with Coenzyme Q (e.g., CoQ10) or a curcuminoid, such as curcumin.

Tocopherols and other antioxidants and cofactors. In some embodiments of the invention a tocopherol, such as alpha-, beta-, gamma- or delta-tocopherol, mixtures thereof, or other antioxidants such as tocotrienols, resveratrol or other stilbenoids such as pterostilbene, retinoids and carotenes including Vitamin A, beta carotene, and alpha-carotene, astaxanthin, canthaxanthin, lutein, lycopene, and zeaxanthin, natural phenols including flavonoids, silymarin, xanthones, eugenol, phenolic acids, lipoic acid, acetylcysteine, uric acid, carotenes, glutathione, catalase, superoxide dismutase, manganese, selenium, may be included as a payload molecule or as part of a payload in a hierarchical aluminosilica of the invention. These may be included in an amount sufficient to exhibit a therapeutic antioxidant activity when delivered to a target site.

ZSM-5. Zeolite Socony Mobil-5 (framework type MFI from ZSM-5 (five)), is an aluminosilicate zeolite belonging to the pentasil family of zeolites. Its chemical formula is $Na_nAl_nSi_{96-n}O_{192}.16H_2O$ ($0<n<27$). The term "ZSM-5-80" refers to ZSM-5 having a $SiO_2/Al_2O_3$ ratio of 80. The term "ZSM-5-80 (0.62)" refers to hierarchical ZSM-5-80 which can be produced by treatment with NaOH/CTAB at a ratio of 0.62. In some instances, a ZSM-5 or hierarchical ZSM-5 may be indicated as having been steamed or functionalized, e.g. "steamed ZSM-5-80 (0.62)" or "CoQ10-ZSM-5-80 (0.62)-S2". In some embodiments, other kinds of zeolites may be substituted for, or partially substituted for ZSM-5, including small, medium or large pore zeolites selected from the group consisting of mordenite, Beta, HY, ZSM-11, ZSM-12, ZSM-22, and ZSM-23.

A hierarchical aluminosilicate contains both mesopores and micropores, wherein micropores have a diameter of <2 nm and mesopores have a diameter of 2 to 50 nm. A hierarchical aluminosilicate contains both mesopores and micropores, unlike homogenous silica, such as tuned mesoporous silica that typically consists of mesopores. Mesoporous silica is composed of siloxane bonds (Si—O—Si) in an amorphous framework, while the hierarchical aluminosilicates of the present invention are composed on Si—O—Al linkages in a crystalline framework. Compared to mesoporous silica, a hierarchical aluminosilicate has high hydrothermal and steam stability due to presence of aluminum in its framework compared to mesoporous silica. This stability can facilitate antioxidant loading and stability. For example, while curcumins are relatively stable compared to coenzyme Q10, CoQ10 can be stabilized by loading into a hierarchical platform under an inert atmosphere. Mesoporous silicas have been synthesized using a bottom up approach and not a top-down approach as described herein. Unlike homogenous structured silicas without aluminum (e.g., SBA-15) or layered silicates such as halloysite which is a natural layered hollow tubular material that has an external surface containing siloxane groups and an internal layer containing aluminum hydroxide groups, the hierarchical aluminosilicates of the invention have both silicon and aluminum homogeneously spread across the framework.

The inventors have found that adsorption of CoQ10 depends on external surface area, pore volume and the presence of weak acid sites. Some advantageous ranges for the hierarchical aluminosilicates of the invention include one or more of (i) a $SiO_2/Al_2O_3$ ratio ranging from about 20, 22, 60, 70, 80, 90, 100, 200, 500, 1,000, 1,200 to 1500, (ii) a crystallite size ranging from 0.5, 1, 1.5, 2, 2.5, 3, 3.5, 4, 4.5, to 5, (iii) substantially steam-stability at 600, 650, 700, 750° 800, 850° C. for 2 hrs, (iv) pore sizes ranging from 2.5, 3, 3.5, 4, 4.5, 5.0 nm, (v) pore volume ranging from 0.5, 0.6, 0.7, 0.8, to 0.9 cc/g (vi) BET external surface area ranging from 200, 300, 400, 500, 600, 700, 800, 900, 1,000, 1,100, 1,200 m²/g, (vii) a total acidity ranging from 0.04, 0.05, 0.06, 0.07, 0.08, 0.09, 0.1, 0.2, 0.3, 0.4, 0.5, 0.6, 0.7, 0.8, 0.9, 1.0, 1.1, 1.2 to 1.3 mmole/gr, and/or (viii) weak surface acidity wherein the weak acid sites represent from 15, 20, 25, 30, 35, 40, 45, 50, 55, 60, 65, 70-75% of the total acid sites. These ranges include all intermediate values. As described herein, selection of two or more of these parameters may additively or synergistically increase CoQ10 or curcuminoid loading.

Figure 6:
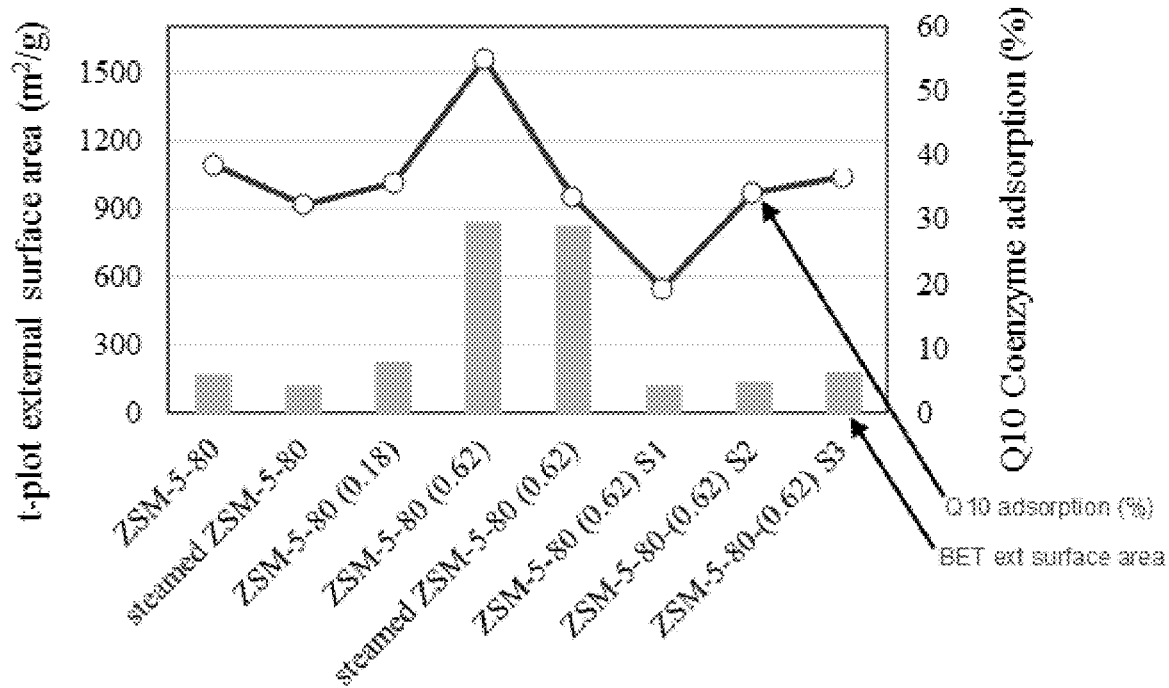
FIG. 6. Shows influence of external surface area of ZSM-5-80 and hierarchical aluminosilicates on the adsorption of CoQ10.

In some embodiments, a hierarchical aluminosilicate, such as ZSM-5-80 (0.62) is not steam-treated and/or not surface functionalized to increase its adsorption of CoQ10 as shown by FIG. 6. In other embodiments, a hierarchical aluminosilicate, such as ZSM-5-80 (0.62) may be steam-treated or functionalized under conditions that do not reduce adsorption of CoQ10 below 35, 30, 25 or 20% or which do not reduce adsorption of the untreated aluminosilicate by more than 10, 20, 30, 40 or 50% after steam treatment.

The acid sites may be determined by $NH_3$-temperature programmed desorption (TPD) analysis where for a weak site $NH_3$ desorbs between 100-250° C., moderate acid sites between >250-350° C. and strong acid sites between >350-550° C.

While not being bound to any particular theory or explanation, it is believed that the hierarchical aluminosilicate of the invention coordinates with electron-rich CoQ10 through hydrogen binding and electrostatic attraction rather than a physical adsorption process and that proton sites are required to coordinate with quinone structure of CoQ10, while weak Lewis acid sites coordinate with electron rich isoprene units.

A top-down approach involves the removal of zeolite framework $Al^{3+}$ atoms by steam or acid treatment or removal of $Si^{4+}$ atoms by treatment with a base. An example of a top-down approach is given by Losch, et al., *Mesoporous ZSM-5 zeolites in acid catalysis: Top_down vs. Bottom-up approach*, 26 Jul. 2017, https://_lib.dr.iastate.edu/cgi/viewcontent.cgi?article=1323&context=cbe_pubstop (last accessed Oct. 16, 2018, incorporated by reference).

Both methods can produce hierarchical silica. However, a proportion of zeolitic formation varies with each process. Top down approach involves dissolution of ZSM-5 crystal in alkaline condition, such condition controls the formation of ZSM-5/MCM-41 composite can be controlled depending on the alkaline solution concentrations (for example 0.2 M NaOH dissolves less ZSM-5 crystal so less hierarchical, 0.7 M NaOH dissolves more ZSM-5 and more hierarchical etc.)., while bottom up approach involves systematic building of framework, where $Al^{3+}$ incorporate into the framework is more favored than extra framework aluminum framework). In bottom up approach, zeolitic layer formation occurs rather than composite.

NaOH/CTAB ratio. A zeolite, such as ZSM-5, may be treated with a solution containing sodium hydroxide (NaOH) and quaternary trimethylammonium cations (CTAB) at a ratio ranging from 0.1 to 1.0, such as at 0.09, 0.1, 0.18, 0.2, 0.3, 0.4, 0.5, 0.6, 0.62, 0.7, 0.8, 0.9, or 1.0, preferably from 0.09 to 0.90. A hydrothermal heating temperature during dissolution preferably ranges from 80, 90, 100, 110, 120, 130, 140 to 150° C. and heating time preferably ranges from 2, 4, 6, 8, 10, 12, 14, 16, 18, 20, 22 to 24 hrs.

Antioxidant compositions. An antioxidant composition may contain one or more antioxidants, such as CoQ10, curcumin or ascorbic acid, and one or more hierarchical aluminosilicates, such as ZSM-5-80 (0.62). It may also include other silica carriers, such as those described herein and other excipients, adjuvants or carriers including medium chain triglycerides, ingestible oils such as coconut oil, soybean oil, canola oil, olive oil, or other vegetable oils, water, hydroxpropylcellulose, gelatin, or surfactants, such as lecithin or a polysorbate. It may be formulated in a form suitable for administration including as a pill, tablet, capsule, gel caplet, soft gel, lozenge, cream, rinse, ointment, gel, paste, water-based cream, emulsions, serum, spray, suppository, ovules, powder, mist, aerosol or other inhalable form, or transdermal patch. It may also be formulated as part of a drink, drink or shake mix or food, or animal feed. In some embodiments, a composition may be formulated for administration by a non-oral, parenteral route including into or around a target site, such as an organ, tissue or tumor, into the lungs or respiratory system, into the brain or spinal column, intravenously, intraperitoneally, intramuscularly, onto a mucous membrane, subcutaneously, intradermally, and topically.

A composition of the invention may contain other active ingredients besides CoQ10, curcumin, such as vitamins, minerals or other nutritional supplements including but not limited to vitamin A, vitamin B1, vitamin B2, vitamin B3, vitamin B5, vitamin B6, vitamin B12, folic acid, vitamin C, vitamin D, vitamin E, vitamin H, L-carnitine, acetyl-L-carnosine, carnosine, trimethyl glycine, grape seed extract, calcium, magnesium potassium, zinc, selenium, selenium, fluorine, phosphorus, iron, and iodine, omega-3 fatty acids, EPA, DHA, omega-6 fatty acids, one or more of the twenty conventional amino acids or selenomethionine, herbal extracts, theophylline, caffeine, or aspirin or other NSAID. An antioxidant may be coated with an acid-resistant coating so as to pass through the stomach and be released in the small intestine.

Subjects. A subject receiving a pharmaceutical preparation containing a hierarchical aluminosilicate and antioxidant as disclosed herein is preferably a human, but may be an animal, preferably a domesticated animal, including avians (e.g., chickens, turkey, geese, ducks, parrots and other pet birds, falcons, hawks, eagles, and other birds of prey) and mammals (e.g., horses, cows, sheep, goats, camels, llamas, pigs; pets such as dogs, cats, rodents). A human subject may be male or female, at least 0, 1, 5, 10, 15, 20, 25, 30, 35, 40, 45, 50, 55, 60, 65, 70, 75, 80, 85, 90, 95 or 100 years old. In some embodiments, a subject may be a pregnant woman or a woman attempting a pregnancy.

Subjects in need of treatment with an antioxidant such as CoQ10 or curcumin include those at risk of, or those suffering from a disease, disorder or condition that would be ameliorated by reduction in free radicals or by other biological activity of the antioxidant. Subjects include those with inflammatory diseases or conditions, those having cardiovascular disease, those suffering from liver toxicity or other toxicosis, Huntington's disease, male infertility, migraine headaches, statin myopathy, cancer, dental disease, and those taking drugs such as statins or beta blockers that reduce synthesis of CoQ10 or other natural antioxidants or reduce serum levels of antioxidants like CoQ10. A subject may also be someone being treated with an anticancer drugs, such as any drug described by https://_www.cancer.gov/about-cancer/treatment/drugs (last accessed Sep. 21, 2018, incorporated by reference). Subjects also include those with below normal levels of CoQ10, ascorbic acid, tocopherols or glutathione in their blood or those undergoing oxidative stress, including those exposed to inflammatory microorganisms, allergens, toxins, other chemicals, or radiation.

Drug delivery may be accomplished by loading a hierarchical aluminosilicate according antioxidant or combination of antioxidants. As shown herein hierarchical nanocomposites suitable as nanocarriers were produced using different NaOH/CTAB ratios 0.18 and 0.62 over ZSM-5 ($SiO_2$/$Al_2O_3$=22-27) of different crystal sizes (0.5 μm, 2.0 μm and 3.0 μm) and different $SiO_2$/$Al_2O_3$ ratios (23, 80, 280 and 1500) through top-down approach. Reassembly of nano ZSM-5 into hierarchical composite was found to exhibit an ordered/disordered hexagonal mesophase depending on alkaline treated ZSM-5 crystal sizes and silica to alumina ratios. Phase changes were analyzed using different textural characterizations such as X-ray diffraction, BET surface area, ammonia desorption technique, $^{27}Al$ MAS NMR, and transmission electron microscope. Twenty one different nanoformulations was screened for CoQ10 adsorption and subsequently selected samples were applied for curcumin and ascorbic acid adsorption. Hierarchical ZSM-5 with $SiO_2$/$Al_2O_3$ ratio 80 (ZSM-5-80 (0.62)) was found to be steam stable and optimum with highest Q10 adsorption (55%). The adsorption influence over different crystal size and silica to alumina ratios, clearly showed the dependency over synergistic action of textural characteristics such as external surface area, pore volume, and weak acidity. The structured nanosupports with pore sizes between 3-4.0 nm were found to exhibit highest CoQ10 adsorption. The inventors found that nanomaterial treated with a NaOH/CTAB ratio of 0.18 contained micropores as confirmed through t-blotting of micropore surface area. However, at a NaOH/CTAB ratio of 0.62 no micropores were observed by t-blotting. At a low detection level the nitrogen adsorption technique is not suitable to measure micropore surface area, so while it is present in a lesser amount in samples treated with a NaOH/CTAB ratio of 0.62, it is not detected by this technique. On the other hand, a suitable analysis can be obtained using an argon adsorption technique and presence of hierarchical micropores is clearly shown by TEM analysis.

Hydrothermal stability of surface area and porosity of the hierarchical nanocomposites may be assessed using steam, such as by treatment with 100% water steam at 700° C. or 750° C. for two hours.

Functionalization with silanes. A hierarchical silica according to the invention, such as ZSM-5-80 (0.62) can be functionalized using different types of silanes such as 3-aminopropyltriethyoxysilane, tetraethylene tetramine, and N-[-3-trimethoxysilyl)propyl]aniline silane.

Composite particles. A hierarchical silica according to the invention may be impregnated with a metal oxide or mixture of metal oxides, such as with gold, titanium or with superparamagnetic iron oxide nanoparticles (SPIONS) to impart catalytic or diagnostic functionality.

SPION or Superparamagnetic iron oxide nanoparticles. SPIONs are composed of magnetite or iron oxide which is degradable in the body and non-toxic compared to other magnetic materials such as cobalt and nickel. The main forms of magnetite are $Fe_3O_4$ and its oxidized form maghemite or $\gamma$-$Fe_2O_3$. SPIONs may be produced by methods known in the art, for example, as described by Sun et al., J, American Chemical Society, 2002, 124, 8204 (incorporated by reference). SPIONs may comprise one or more coatings or may be incorporated along with a hierarchical aluminosilicate into micelles or liposomes to enhance their pharmacokinetic properties including biological half-life, biocompatibility, and targeting. In some embodiments, the compositions of the invention contain SPIONs of a size compatible with in vivo administration and desired targeting functionality.

Some representative SPION particle sizes range from about 0.5, 1, 2, 5, 10, 20, 30, 40, 50, or 60 nm. A composition of the invention may contain a single size or single size distribution of SPIONs or may contain two or more sizes or size distributions. For example, various mixtures of large SPIONs ranging from about 10 to 60 nm in average size and small SPIONs ranging in size from about 0.5 to 22 nm may be used. Mixtures of SPIONs of different sizes permit tuning of a biological responses or imaging functions. In some embodiments, a coprecipitation technique can be followed to form metal oxide composite with Ni or Cu or Mn and Co nanoparticle to form respective $MFe_2O_4$ to enhance imaging capacity by increasing magnetization property.

In some embodiments the core of the SPIONs may be magnetite which is covered with one or more shells, for example, a polymer shell or a gold or metal shell. SPIONs may also be incorporated into, or coated with, one or more polymers including smart, pH-sensitive, or temperature-sensitive polymers.

Functionalized super paramagnetic iron oxide nanoparticles (SPIONs) may be used in accordance with one or more embodiments of the invention, for example, a SPION may be functionalized with a targeting ligand such as an antibody that binds to a tumor-associated antigen or other target tissue. In some embodiments SPIONs may be conjugated to targeting moieties such as ligands that bind to, or agents that are internalized by, target molecules, receptors, cells or tissues.

The content of SPIONS, hierarchical aluminosilicate, and antioxidant, such as curcumin, CoQ10 or ascorbic acid, in a composition according to the invention may be selected based on its intended use. However, some general content ranges for these components include from about 1, 2, 3, 4, 5, 6, 7, 8, 9, 10, 11, 12, 13, 14, 15, 16, 17, 18, 19 to about 20 wt % SPIONS; from about 80, 81, 82, 83, 84, 85, 86, 87, 88, 89, 90, 91, 92, 93, 95 to about 95 wt % hierarchical aluminosilicate; or from about 80, 81, 82, 83, 84, 85, 86, 87, 88, 89, 90, 91, 92, 93, 95 to about 95 wt % hierarchical aluminosilicate bound to antioxidant. In some embodiments one or more other active ingredients may be incorporated into a hierarchical aluminosilicate-antioxidant composition, or such a composition that further includes SPIONs, for example, one or more anticancer drugs, such as any drug described by https://_www.cancer.gov/about-cancer/treatment/drugs (last accessed Sep. 21, 2018, incorporated by reference). Such compositions may optionally be targeted to a particular organ, tissue or cancer type, for example, by conjugation or admixture with drugs specific for an organ, tissue or cancer type.

Tissue imaging and/or drug delivery. The hierarchical aluminosilicate of the invention can be further impregnated or mixed with metal oxides such as gold, titanium and superparamagnetic iron oxide nanoparticles (termed as SPIONs). For example, the hierarchical aluminosilica of the invention can modified with SPIONS or with $NiFe_2O_4$ nanoparticles For tumor or tissue imaging, a hierarchical aluminosilicate like a ZSM-5-80 (0.62) sample can further be modified with $NiFe_2O_4$ nanoparticles for biomedical uses such as tumor imaging and drug delivery application. The experimental study showed that impregnation of iron oxide and nickel oxide using coimpregnation technique tends to form $NiFe_2O_4$ nanoparticles over hierarchical ZSM-5.

The ZSM-5 $SiO_2/Al_2O_3$ ratio can be varied from of 80, 100, 200, 300, 400, 500, 1,000, 1,500, 2,000, 2,500, to 3,000 (or any intermediate value within this range), while $NiFe_2O_4$ impregnation weight percentage can be varied from 5, 10, 15, 20, 25, 30, 35, 40, 45-50 wt. %. The magnetic property and nanoparticle formation can be measured using vibrating sample magnetometry and X-ray diffraction techniques. The surface area and morphological variations was measured using BET surface area, SEM and TEM analysis.

Figure 12:
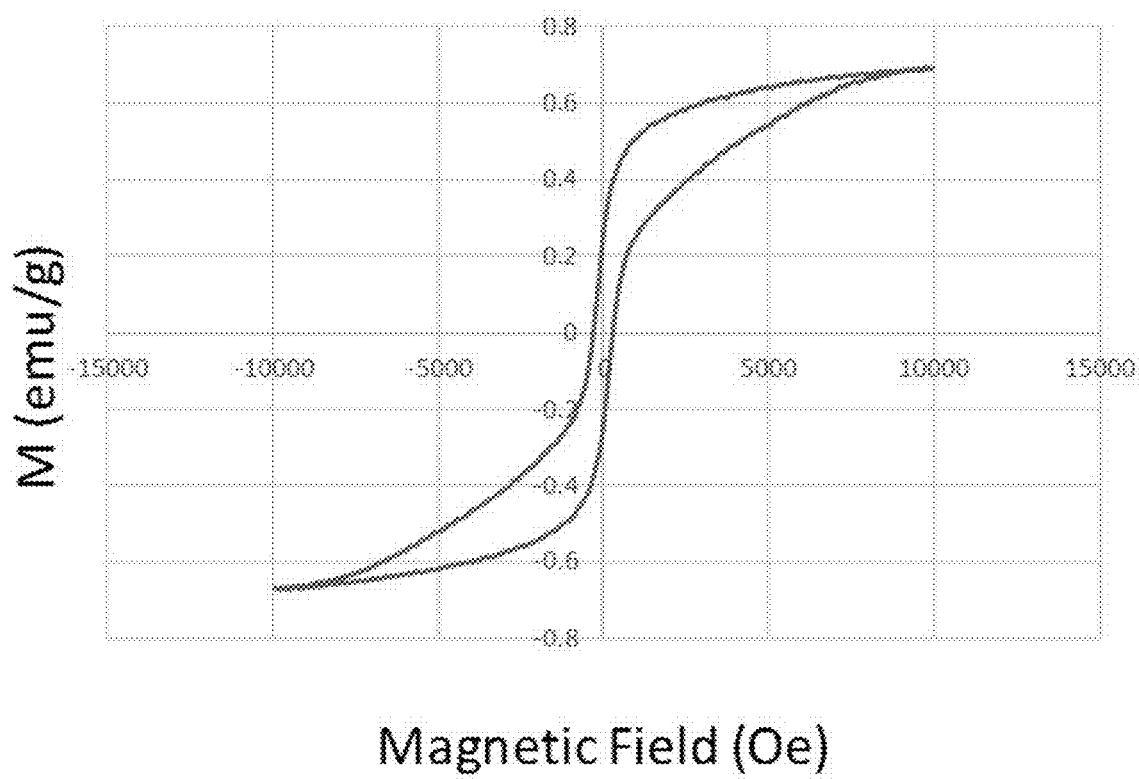
FIG. 12. VSM analysis of 30% $NiFe_2O_4$/ZSM-5-80 (0.62).

Spinel ferrite loading. In some embodiments, the aluminosilicate of present invention can be loaded with spinel ferrite to generate magnetically active nanocomposite that can be used for dual purposes of a drug or biological such as for delivery CoQ10 as well as for imaging, for example, tumor imaging. An example of spinel ferrite loading is described below. A 2 g sample was prepared; for 30% loading of $CuFe_2O_4$ 0.17 g of Cu, 0.3 g of iron nitrate and 1.4 g of ZSM-5-80 (0.62) was taken in the crucible, calcined at 850 C for 6 h; then the mixture was ground for 15 min. FIG. 12 shows the magnetic property of 30 wt % spinel ferrite loaded over a ZSM-5-80 (0.62) aluminosilicate nanocarrier with $SiO_2/Al_2O_3$ ratio 80.

Mixed metal oxide loading. The same nanocarrier can be loaded with mixed metal oxides including nickel oxides (e.g., NiO), iron oxides (e.g., $Fe_2O_3$) in presence of bismuth (Bi), tantalum (Ta), and/or niobium (Ni) to form binary metal oxide species for oxidative dehydrogenation of alkanes such as propane to propylene, n-butane to butenes, etc.

Oxidative dehydrogenation of light alkanes may be performed using a hierarchical ZSM-5 according to the invention, for example, propane or butane may be dehydrogenated to produce propylene and butenes, respectively. Hierarchical ZSM-5 with silica to alumina ratios between 80, 100, 200, 300, 400, 500, 1,000, 1,500, 2,000, 2,500, to 3,000 (or any intermediate value within this range), can further be modified with nickel (NiO), iron oxide ($Fe_2O_3$) in presence of bismuth, tantalum, niobium to form binary metal oxide species for oxidative dehydrogenation of alkanes such as propane to propylene, n-butane to butenes, etc. The weight percentage of nickel oxide can range from 10, 11, 12, 13, 14, 15, 16, 17, 18, 19, or 20 wt. %, bismuth can be 10, 15, 20, 25-30 wt. %, while $Fe_2O_3$ can be between 2, 3, 4, and 5 wt. %, respectively.

Functionalization. The aluminosilicate of the invention may be further functionalized. For example, ZSM-5-80 (0.62) can be functionalized using a silane such as 3-aminopropyltriethoxysilane, tetraethylene tetramine, or N-[-3-trimethoxysilyl)propyl]aniline silane. Silanes may be used as coupling agents for glasses and polymers, as adhesion promoters, as cross-linking and dispersing agents, or for hydrophobization. In other embodiments, a targeting agent, such as an antibody that recognizes a particular antigen, such as a tumor antigen, may be bound to or incorporated into a hierarchical aluminosilicate of the invention. The biocompatibility of a hierarchical aluminosilicate can be enhanced with encapsulation of biocompatible polymers like chitosan, poly (D,L-lactide-co-glycolide), or polyethylene glycol.

The invention includes but is not limited to the following embodiments. A composition including at least one antioxidant, such as CoQ10 or curcumin and a hierarchical aluminosilicate having an $SiO_2/Al_2O_3$ ratio ranging from 20, 22, 30, 40, 50, 60, 70, 80, 90, 100, 120, 150, 200, 220, 250, 300, 350, 400, 450, 500, 550, 600, 650, 700, 750, 800, 850, 900, 950, 1,000, 1,050, 1,100, 1,150, 1,200, 1,250, 1,300, 1350, 1,400, 1,450 to 1,500 and an external surface area of at least 200, 300, 400, 500, 600, 700, 800, 900, 1,000, 1,100 to 1,200 $m^2/g$, wherein the at least one antioxidant is adsorbed to the hierarchical aluminosilicate, and wherein said composition comprises at least 10, 20, 30, 40, 50, 60, 70, 75 or 80 wt % of the at least one antioxidant based on the total weight of the composition. In some embodiments the composition will include a hierarchical aluminosilicate that has a pore size ranging from 2.5, 3, 3.5, 4, 4.5, to 5 μm and/or a pore volume ranging from 0.3, 0.4, 0.5, 0.6, 0.7, 0.8, 0.9 to 1.0 cc/g. In some embodiments, the hierarchical aluminosilicate has a stable zeolitic framework that retains at least 70, 75, 80, 85, 90, 95 or >95% of its presteaming external surface area after water steaming at 700° C. of 750° C. for 2 hours. In some other embodiments, the hierarchical aluminosilicate has a weak acidity ranging from 0.02, 0.025, 0.0275, 0.03, 0.035, 0.04, 0.05, 0.055 mmol/g and a total acidity that does not exceed 0.1, 0.11, 0.12, to 0.13 mmol/g and/or comprises weak acid sites, wherein the weak acid sites represent from 15, 20, 25, 30, 35, 40, 45, 50, 55, 60, 65, 70 to 75% of the total acid sites.

In some embodiments a composition of the invention will contain an antioxidant that is CoQ or CoQ10 and in others it will contain a curcumin or another curcuminoid. In still others it may contain ascorbic acid, a mineral ascorbate or a fat-soluble ascorbate. Other embodiments may include a mixture of one or more antioxidants, such as a mixture of CoQ10 and curcumin and vitamin C. In some embodiments, the amount of one or more antioxidants such as CoQ10, curcumin or vitamin C may range from at least 10, 20, 30, 40, 50, 60, 70 or 80 wt % of the total weight of the composition.

In some embodiments, the hierarchical aluminosilicate is ZSM-5, the antioxidant is Coenzyme Q10 which is in an amorphous, non-crystalline form.

In other embodiments, the composition includes a hierarchical aluminosilicate that is produced by a top-down methodology comprising treating ZSM-5 with NaOH/CTAB at a ratio between 0.1, 0.2, 0.3, 0.4, 0.5, 0.6, 0.7, 0.8, 0.9 to 1.0, neutralizing the treated ZSM-5, drying the neutralized ZSM-5, and calcining the dried ZSM-5 product at a temperature of 500, 550, 600, 650, 700, 750, 800, 850, or 900° C.

A composition of the invention may further comprise as an ingredient or coating chitosan, polyacrylic acid, PLGA, or another biocompatible polymer or agent. In other embodiments a composition of the invention may further comprise SPIONs.

Another embodiment of the invention is directed to a method for making a hierarchical aluminosilicate including treating ZSM-5 with a solution of NaOH/CTAB, recovering the treated ZSM-5, and calcining the treated ZSM-5 for a time and under conditions suitable for producing a hierarchical aluminosilicate. In some embodiments, this method involves treating ZSM-5 at an alkaline pH with a solution of NaOH/CTAB present at a ratio ranging from 0.1, 0.2, 0.3, 0.4, 0.5, 0.6, 0.7, 0.8, 0.9 to 1.0 at a temperature ranging from 70, 80, 90, 100, 110, 120, 130 to 140° C. for a time sufficient to break ZSM-5 crystals with or without stirring, adjusting the pH to a range from 8, 8.5, 9, 9.5 to 10 and stirring the solution for at least 2, 4, 6, 8, 10, or 12 hours, aging the resulting solution at a temperature ranging from 70, 80, 90, 100, 110, 120, 130 to 140° C. for at least 2, 4, 6, 8, 10 or 12 hours, filtering the resulting solution and washing the recovered material with water or an aqueous solution until a close to neutral pH of is attained, for example a pH of 6.5, 6.7, 6.75, 6.8, 6.9, 7.0, 7.1, 7.2, 7.25, or 7.5, and drying the recovered material; and wherein the calcining comprises calcining the dried recovered material at a temperature ranging from 400, 500, 600, 700, 800, 900 or 1,000° C. to produce a white powder, ion-exchanging the white powder with NH$_4$Cl and recovering an ion-exchanged powder, and calcining the ion-exchanged powder at a temperature ranging from 400, 500, 600, 700, 800, 900 or 1,000° C., thereby producing the hierarchical aluminosilicate.

In some embodiments of this method the ZSM-5 has a crystal size ranging from 0.5, 1, 1.5, 2, 2.5, 3, 3.5, 4, 4.5, 5.0, 5.5, to 6 μm and/or the ZSM-5 has a SiO$_2$/Al$_2$O$_3$ ratio ranging from 20, 50, 100, 200, 500, 1,000, 1,100, 1,200, 1,300, 1,400, 1,500 to 1,600. In other embodiments the ZSM-5 is ZSM-5-80 or another aluminosilicate has a ratio of SiO$_2$:Al$_2$O$_3$ ranging from about 60, 65, 70, 75, 80, 85, 90, 95 or 100 and the ratio of NaOH/CTAB ranges from 0.5, 0.55, 0.6, 0.65, 0.7 to 0.75. In other embodiments, this method will further including functionalizing the hierarchical aluminosilicate with a silane and/or will further include loading Coenzyme Q, a curcuminoid, vitamin C, or at least one other antioxidant by equilibrium adsorption.

In other embodiments of this method, it will further include incorporating into the hierarchical aluminosilicate, nickel oxide (NiO) or iron oxide (Fe$_2$O$_3$) in the presence of bismuth, tantalum, or niobium to form a binary metal oxide species that oxidatively dehydrogenates alkanes. Another embodiment of the invention is directed to a method for oxidatively dehydrogenating an alkane using a hierarchical aluminosilicate containing these metal oxides by contacting the alkane with a hierarchical aluminosilicate containing these metal oxides.

EXAMPLES

The following examples illustrate various aspects of the present invention. They are not to be construed to limit the claims in any manner whatsoever.

The parent ZSM-5-23 (0.5 μm crystal size), ZSM-5-80, ZSM-5-280 were purchased from Zeolyst International. ZSM-5-22 (2 μm crystal size) and ZSM-5-27 (3 μm crystal size) were purchased from CATAL and ZSM-5-1500 was obtained from Tosoh, Japan. The antioxidant CoQ10 (≥98%), curcumin, and ascorbic acid were purchased from Sigma-Aldrich.

Figure 14:
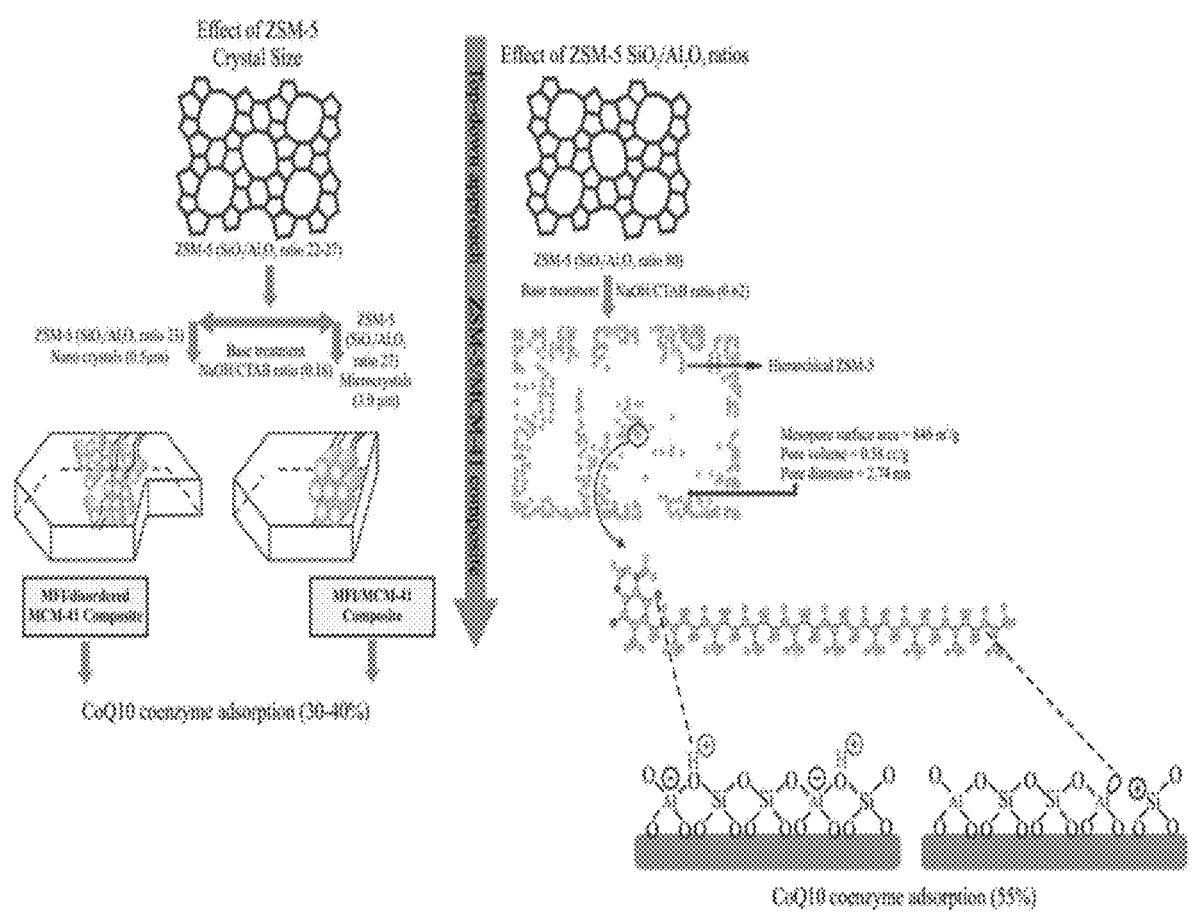
FIG. 14 (Scheme 2) depicts top-down approach showing the effects of crystal size and silica to alumina ratios on hierarchical aluminosilicate formation and CoQ10 coenzyme adsorption.
Figure 15B:
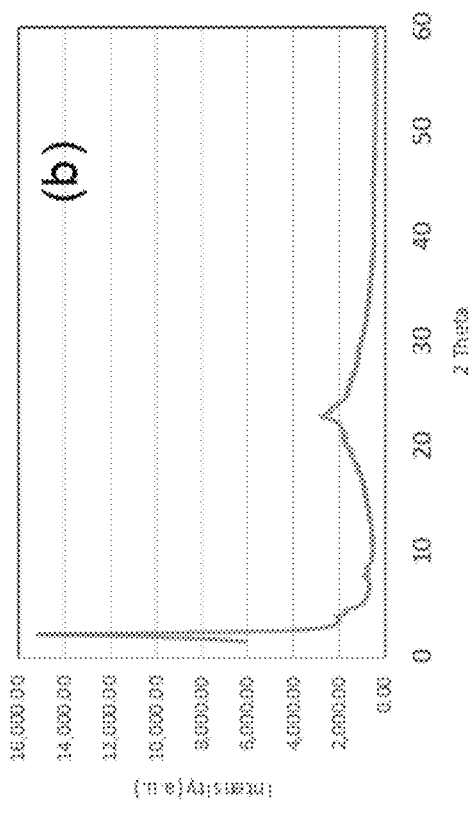
FIGS. 15A-15D show the XRD diffraction spectra of CoQ10 (FIG. 15A), ZSM-5-80 (0.62)(FIG. 15B), ZSM-5-80 (0.62)-S1 (FIG. 15C) and ZSM-5-80 (0.62)-S2 (FIG. 15D), respectively.
Figure 15D:
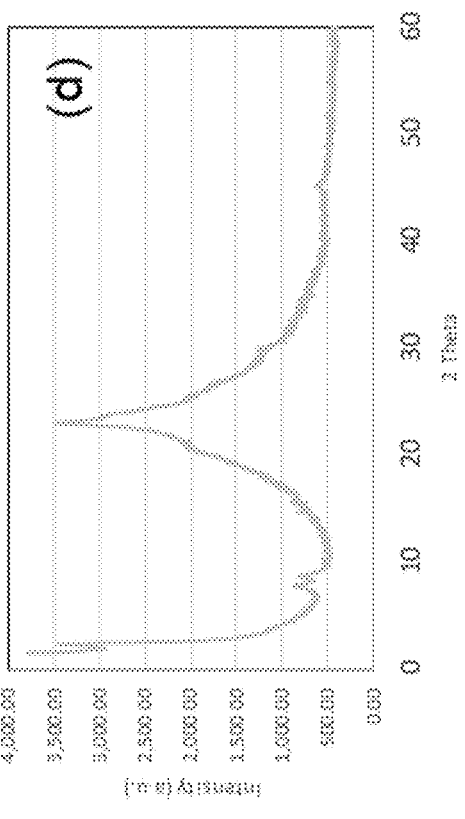
Figure 15A:
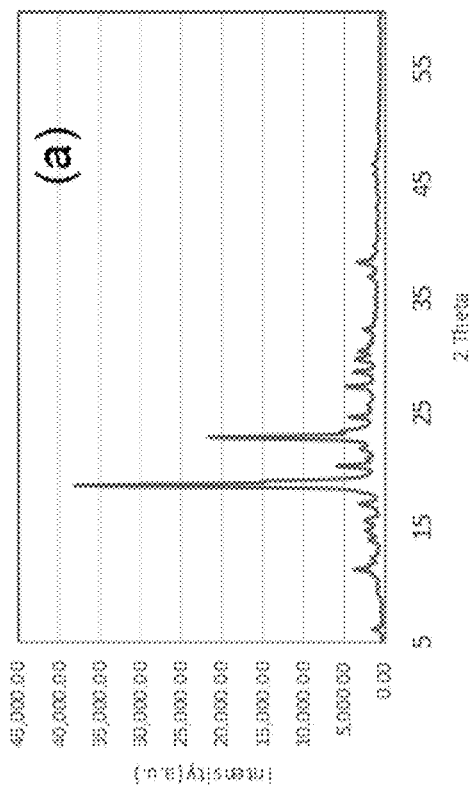
Figure 15C:
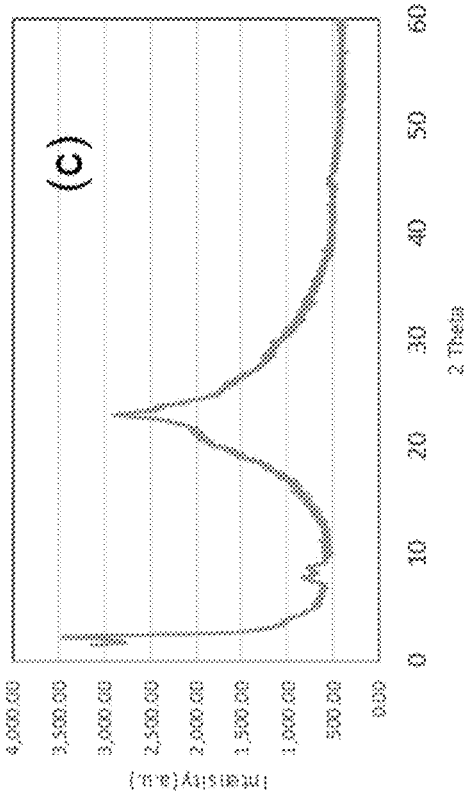

Preparation of hierarchical aluminosilicate nanocarriers of SiO$_2$/Al$_2$O$_3$ ratio 23 and 27 with different crystal size of 0.5 μm and 3 μm, respectively. Hierarchical mesoaluminosilicates were prepared using ZSM-5 with similar SiO$_2$/Al$_2$O$_3$ ratio of 23 and 27 but with different crystal sizes of 0.5 μm and 3.0 μm through top-down methodology as depicted by Scheme 2 (FIG. 14). The crystals were initially broken by heating them at 100° C. in static hydrothermal conditions under NaOH/CTAB ratios of 0.18 and 0.62, respectively, to produce a turbid white solution.

In this procedure 2 g of ZSM-5 (23) or ZSM-5 (27) was dissolved in 60 ml of 0.2 M NaOH or 0.7 M NaOH solution. However, the weight of the ZSM-5 can be varied between 0.5, 1, 1.5, 2, 2.5, 3, 3.5 to 4.0 grams and the alkaline concentration can be varied in a range from 0.1, 0.2, 0.3, 0.4, 0.5, 0.6, 0.7, 0.8, 0.9 to 1.0 M NaOH or to any intermediate value within these ranges.

The turbid white solution was then pH adjusted to pH 9-10 and stirred for 24 h at 500 rpm under ambient conditions and then hydrothermally aged at 100° C. for 24 h to obtain a milky solution.

The milky solution was filtered, washed with distilled water until the pH became neutral, dried and calcined for 6 h at 550° C. with a heating rate of 10° C./min to obtain a white powder.

The white powder was ion-exchanged there times using 1.0 M NH$_4$Cl solution (1 g per 10 ml) and then calcined again at 500° C. for 2 h thus producing two series of three hierarchical aluminosilicates ZSM-5 (0.18) and three hierarchical aluminosilicates ZSM-5 (0.62) from ZSM-5 having three different crystal sizes.

Preparation of hierarchical aluminosilicate nanocarriers with different SiO$_2$/Al$_2$O$_3$ ratios of 23, 80, 280 and 1,500 using NaOH/CTAB ratio 0.18 and 0.62, respectively Hierarchical mesoaluminosilicates having different SiO$_2$/Al$_2$O$_3$ ratios were prepared through top-down methodology. ZSM-5 crystals having of SiO$_2$/Al$_2$O$_3$ ratios of 23, 80, 280 or 1,500 were initially broken by heating them at 100° C. in static hydrothermal conditions under NaOH/CTAB ratio of 0.18 and 0.62, respectively, to produce a turbid white solution.

The turbid white solution was then pH adjusted to pH 9-10 and stirred for 24 h at 500 rpm under ambient conditions and then hydrothermally aged at 100° C. for 24 h to obtain a milky solution.

The milky solution was filtered, washed with distilled water until the pH became neutral, dried and calcined for 6 h at 550° C. with a heating rate of 10° C./min to obtain a white powder.

The white powder was ion-exchanged there times using 1.0 M $NH_4Cl$ solution (1 g per 100 ml) and then calcined again at 500° C. for 2 h, thus producing two series of four hierarchical aluminosilicates ZSM-5 (0.18) and four hierarchical aluminosilicates ZSM-5 (0.62) having different $SiO_2/Al_2O_3$ ratios.

Hierarchical aluminosilicate nanocarriers were steamed with 100% water at 700° C. and 750° C., respectively. As described by FIG. 2 below, in order to develop an effective antioxidant nanocarrier, a robust stable zeolitic framework is required. Steaming is to de-alumination process and structural deformity or stability of nanocarriers can be characterized by the extent of structural retention with steaming process. A steaming process may also realign the active species of the framework and enhance adsorption of active species. Steaming of zeolite tends to remove the framework aluminum and reduce the acidity of Bronsted acid sites.

Functionalization using silanes. ZSM-5-80 (0.62) functionalization was carried out in inert atmosphere using Schenk line apparatus setup using 3-aminopropyltriethyoxysilane, tetraethylene tetramine, and N-[-3-trimethoxysilyl)propyl]aniline silane designated as ZSM-5-80 (0.62)-S1, ZSM-5-80 (0.62)-S2 and ZSM-5-80 (0.62)-S3, respectively. In brief, ZSM-5-80 (0.62)-S1 was synthesized by treating 2.2 g of ZSM-5-80 (0.62) support with 3-aminopropyltriethyoxysilane (3.3 ml) in presence of anhydrous toluene (220 ml) solvent. The solution mixture was refluxed for 2 h and then filtered and vacuum dried for 2 h. A similar protocol followed for functionalization of other silanes.

Silica-type mesocellular foam designated as Si-MSU-Foam, aluminum containing mesocellular foam designated as Al-MSU-Foam, Spherical micron sized silica, was purchased from Sigma Aldrich.

Siliceous SiSBA-16, ULPFDU-12, SiKIT-6, and Silicalite were prepared substantially as described by the inventors' prior publications; Vijaya Ravinayagam and B. Rabindran Jermy, *Studying the loading effect of acidic type antioxidant on amorphous silica nanoparticle carriers*, Journal of Nanoparticle Research, 19 (2017) 190; B Rabindran Jermy, Sadananda Acharya, Vijaya Ravinayagam, Hajer Saleh Alghamdi, Sultan Akhtar, Rehab S Basuwaidan, *Hierarchical mesosilicalite nanoformulation integrated with cisplatin exhibits target-specific efficient anticancer activity*, Appl Nanosci. June 2018, Volume 8, Issue 5, pp 1205-1220, https://_doi.org/10.1007/s13204-018-0786-9. These methods are incorporated by reference to the above-cited publications.

Antioxidant loading technique. A standard solution of 100 ppm Q10 coenzyme was prepared under inert nitrogen atmosphere using 1-butanol as solvent. The sample Q10 coenzyme adsorption process was carried out using 30 mg of aluminosilicate sample in 5 g of 100 ppm of Q10 coenzyme solution under inert condition using Schlenk system equipped with 5 port vacuum manifold along with trap assembly. The solution was stirred for 24 h at room temperature after which the mixture was filtered and washed with 5 ml butanol as a solvent.

Curcumin antioxidant adsorption over different aluminosilicates was carried out through a similar equilibrium adsorption technique, however, methanol was used as a solvent instead of butanol for curcumin adsorption.

Ascorbic acid was loaded in an aqueous medium. After stirring, the solutions were filtered and dried at room temperature. The percentage adsorption was calculated based on the equation:

Percentage of $Q10$ coenzyme adsorption (%)=(Initial $Q10$ conc−Final $Q10$ conc)/Initial $Q10$ conc×100.

The final Q10 concentration was calculated based on the equation:

Final concentration=(Final absorbance value×Initial $Q10$ conc)/Initial absorbance value.

Figure 13:
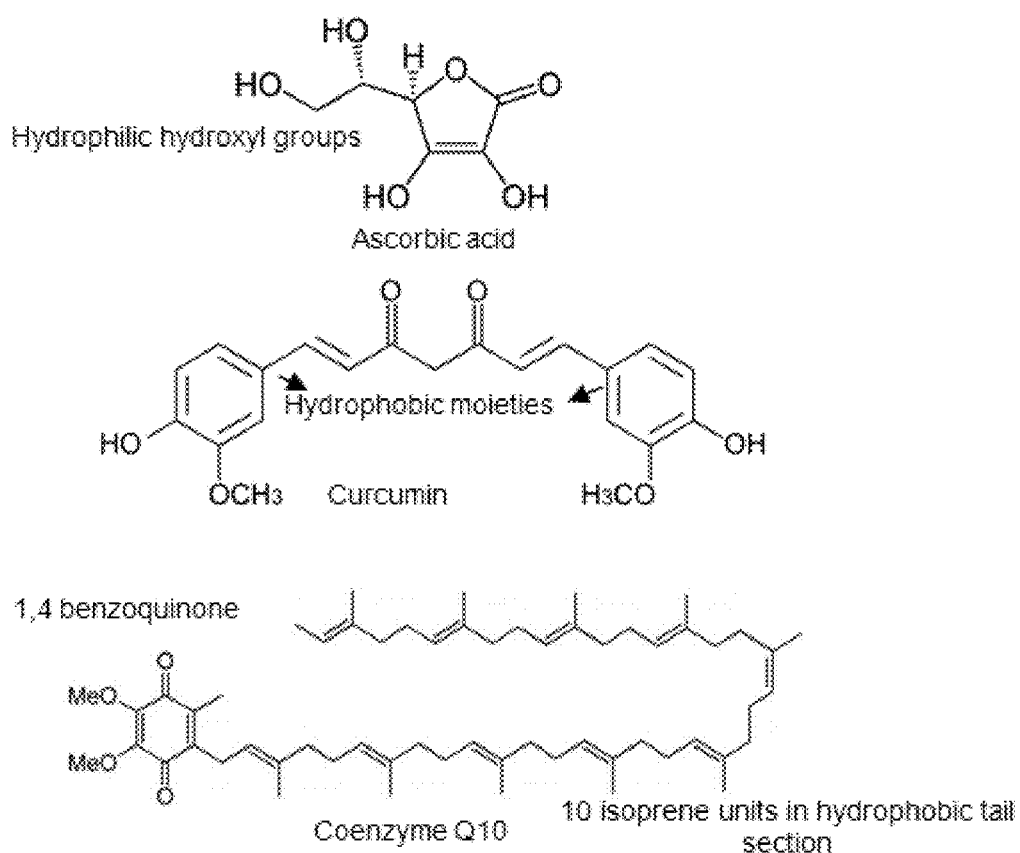
FIG. 13 (Scheme 1) shows structures of ascorbic acid, curcumin and Coenzyme Q10.

The chemical structures of ascorbic acid, curcumin and CoQ10 appear in FIG. 13. As shown there ascorbic acid contains many hydrophilic hydroxyl groups, curcumin contains hydrophobic structures denoted by arrows and CoQ10 has a long hydrophobic tail section having 10 isoprene units.

Characterization of hierarchical aluminosilicates. The micro and meso phases of hierarchical aluminosilicates were analyzed by X-ray diffraction using a Rigaku Multiplex, Japan. Textural characteristics were analyzed using Micromeritics, ASAP 2020, USA. Antioxidant functional groups were identified using an ATR probe by Fourier transform infrared spectroscopy (Perkin Elmer). The external morphology of an aluminosilicate was analyzed using transmission electron microscope (TEM, FEI, Morgagni, Czech Republic). Total acidity was measured using an ammonia desorption technique ($NH_3$-TPD) in BELCAT reactor system, Japan. The aluminosilicate sample (100 mg) was predried and treated in a helium atmosphere at the flow rate of 50 mL/min at 500° C. for 1 h. The aluminosilicates were then treated with helium-ammonia mixture (95/5 vol. %) for 30 min at ambient condition. Physically adsorbed $NH_3$ was removed by purging with helium gas. Then TPD analysis was performed in presence of helium flow of 50 mL/min (10° C./min) using TCD detector. The Al distributions in the parent zeolite, AlMCM-41 and hierarchical samples was determined using $^{27}Al$MAS NMR using JEOL Lambda NMR spectrometer.

Characterization of hierarchical ZSM-5. FIGS. 1A-1D show the variations of hierarchical mesoaluminosilicate formation produce using a top-down methodology with two different NaOH/CTAB ratios of 0.18 and 0.62, respectively. FIG. 1A (a-c) shows the effect of alkaline treatment effect for varying crystal sizes of ZSM-5. ZSM-5-27 with crystal size of 3 μm (c), ZSM-5-22 with crystal size of 2 μm (a) and ZSM-5-23 with crystal size of 0.5 μm (b) were treated with NaOH/CTAB ratio 0.18 and compared the mesostructured formation by maintaining other synthesis protocol constant.

Figure 1B:
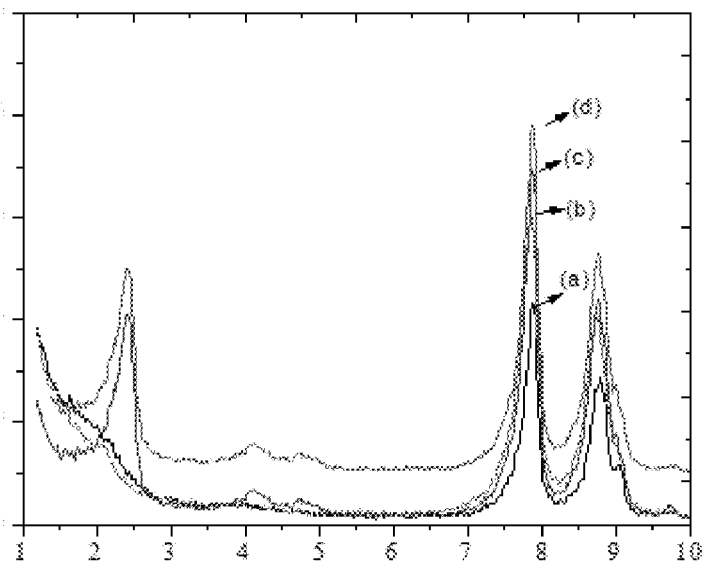
FIG. 1B shows the alkaline treatment effect (NaOH/CTAB ratio 0.18) over ZSM-5 of different silica to alumina ratios: 23 (a), 80 (b), 280 (c) and 1500 (d) over NaOH/CTAB ratios 0.18 and 0.62, respectively.
Figure 1C:
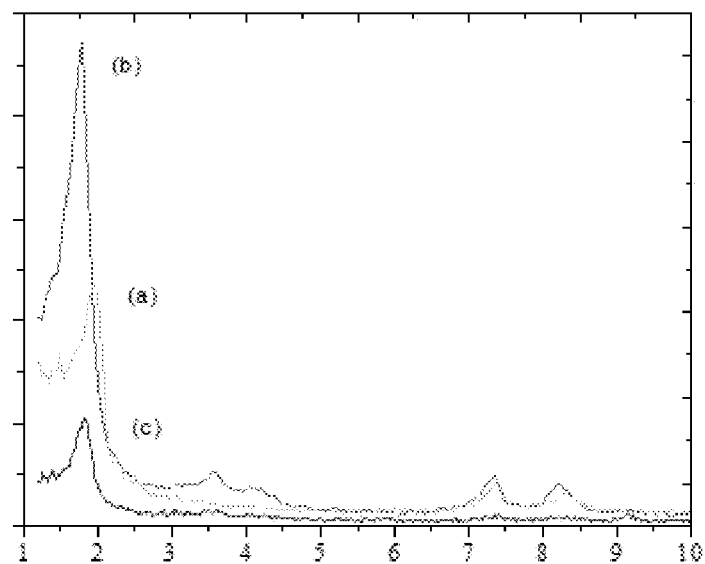
FIG. 1C shows an increased alkaline treatment effect with NaOH/CTAB ratio 0.62 for micro/meso hierarchical formation over ZSM-5 ($SiO_2/Al_2O_3$=22-27) with different crystal sizes 2.0 μm (a), 0.5 μm (b) and 3.0 μm (c).

The caption is based on a silica to alumina ratio so FIG. 1A corresponds to ZSM-5 ($SiO_2/Al_2O_3$ ratio 22), FIG. 1B corresponds to ZSM-5 (SiO2/Al2O3 ratio 23) and FIG. 1C corresponds to ZSM-5 ($SiO_2/Al_2O_3$ ratio 27).

Specifically, after alkaline treatment, the samples were hydrothermally treated at 100° C. in static condition for 24 h, then the disintegrated solution was pH adjusted, aged under the same conditions, filtered, dried and calcined. The textural characteristics are presented in Table 1.

TABLE 1

Textural characteristics of ZSM-5 (SiO$_2$/Al$_2$O$_3$ = 22-27) with different crystal sizes
(0.5 µm, 2.0 µm and 3.0 µm) and SiO$_2$/Al$_2$O$_3$ ratios (23, 80, 280 and 1500)
over NaOH/CTAB ratios 0.18 and 0.62, respectively

| Sample | SiO$_2$/Al$_2$O$_3$ ratio | NaOH/CTAB ratio | Surface area (m$^2$/g) multi | t-plot Micropore area (m$^2$/g) | Pore volume (cc/g) | t-plot Micropore volume (cc/g) | Mesopore volume (cc/g) | Pore size distribution (nm) |
|---|---|---|---|---|---|---|---|---|
| ZSM-5 | 22 | — | 330 | 205 | 0.20 | 0.12 | 0.08 | — |
| ZSM-5 | 23 | — | 342 | 244 | 0.22 | 0.13 | 0.09 | — |
| ZSM-5 | 27 | — | 278 | 170 | 0.20 | 0.12 | 0.08 | — |
| ZSM-5 | 22 | 0.18 | 388 | 199 | 0.33 | 0.10 | 0.23 | 3.39 |
| ZSM-5 | 23 | 0.18 | 347 | 198 | 0.20 | 0.10 | 0.10 | 2.87 |
| ZSM-5 | 27 | 0.18 | 289 | 102 | 0.24 | 0.05 | 0.19 | 3.38 |
| ZSM-5 | 22 | 0.62 | 500 | — | 0.65 | — | 0.65 | 5.20 |
| ZSM-5 | 23 | 0.62 | 629 | — | 0.75 | — | 0.75 | 4.80 |
| ZSM-5 | 27 | 0.62 | 634 | — | 0.55 | 0.01 | 0.54 | 3.46 |
| ZSM-5 | 23 | 0.18 | 347 | 198 | 0.20 | 0.10 | 0.10 | 2.87 |
| ZSM-5 | 80 | 0.18 | 358 | 136 | 0.31 | 0.07 | 0.24 | 3.52 |
| ZSM-5 | 280 | 0.18 | 397 | 121 | 0.30 | 0.06 | 0.24 | 3.02 |
| ZSM-5 | 1500 | 0.18 | 223 | 156 | 0.25 | 0.05 | 0.20 | 2.50 |
| ZSM-5 | 23 | 0.62 | 629 | — | 0.75 | — | 0.75 | 4.80 |
| ZSM-5 | 80 | 0.62 | 779 | 0 | 0.78 | — | 0.78 | 3.91 |
| ZSM-5 | 280 | 0.62 | 902 | 0 | 0.60 | — | 1.07 | 4.75 |
| ZSM-5 | 1500 | 0.62 | 710 | 0 | 0.58 | — | 0.58 | 3.28 |

While some of the ZSM-5 samples have no t-plot micropore volume as determined by the nitrogen adsorption technique, the presence of hierarchical pores is shown by TEM analysis.

Though at similar treatment conditions, three different sizes of ZSM-5 crystals showed formation of secondary network of mesopores and that a clear variation occurs with the extent of hexagonal mesophase formation in the composite. In particular, diffraction pattern showed variable intensity of hexagonal MCM-41 at low angle region (2-5°) and ZSM-5 at higher angle (8-50°) at similar CTAB/NaOH ratio of 0.18, FIG. 1A (a-c). For instance, as shown by FIGS. 1 (a) and (b), ZSM-5-22 with crystal size 2 µm showed MFI/MCM-41 composite formation with hexagonal structured composite with presence of a less intense (100), (110) and (200) peaks but comparatively better than ZSM-5-27 having a 3 µm crystal size. While ZSM-5-23 with crystal size 0.5 µm (c) showed no clear cut (100), (110) and (200) peaks, indicating the formation of disoriented mesophase due to disordered hexagonal originating from nano ZSM-5 particles, FIG. 1A (c). The result shows that even with similar SiO$_2$/Al$_2$O$_3$ ratios, formation of hexagonal MCM-41 as composite with microporous ZSM-5 remains unique and directly depends on the crystal sizes of treated ZSM-5.

FIG. 1B (a)-(d) shows the alkaline treatment effect (NaOH/CTAB ratio 0.18) over ZSM-5 of different silica to alumina ratios 23 (a), 80 (b), 280 (c) and 1,500 (d), respectively.

In case of ZSM-5 with ratio of 23 and 80, absence of peaks corresponding to MCM-41 showed the inefficiency of alkaline to template ratio 0.18, FIG. 1B (a) and (b). However, with ZSM-5 of high silica to alumina ratios such as 280 and 1,500, the diffraction pattern revealed that highly ordered mesostructure formation occurred with a well resolved peaks indexed to (100), (110) and (200), FIG. 1B (c) and (d).

FIG. 1C (a)-(c) shows an increased alkaline treatment effect with NaOH/CTAB ratio 0.62 for micro/meso hierarchical formation over ZSM-5 (SiO$_2$/Al$_2$O$_3$=22-27) with different crystal sizes 0.5 µm (c), 2.0 µm (a) and 3.0 µm (b).

As shown by FIG. 1C the diffraction pattern showed a variable degree of mesostructure formation in response to an increase in the severity of NaOH/CTAB treatment of ZSM-5 having different crystal sizes. ZSM-5-22 showed the highest hexagonal mesoporous formation, followed by ZSM-5-23 and ZSM-5-27, respectively.

Figure 1D:
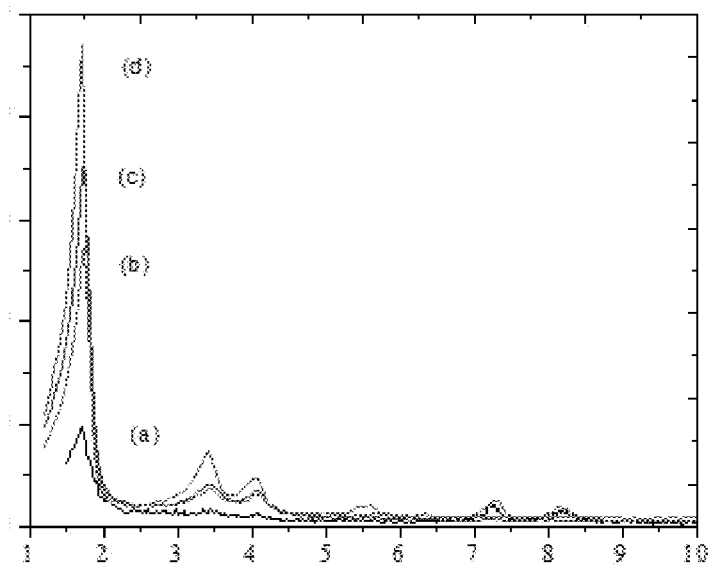
FIG. 1D shows an increased alkaline treatment effect with NaOH/CTAB ratio 0.62 for micro/meso hierarchical formation over ZSM-5 ($SiO_2/Al_2O_3$=22-27) with different $SiO_2/Al_2O_3$ ratios 23 (a), 80 (b), 280 (c) and 1500 (d).

FIG. 1D (a)-(d) show effects of an increase in the severity of NaOH/CTAB treatment of ZSM-5 having SiO$_2$/Al$_2$O$_3$ ratios of 23 (a), 80 (b), 280(c) and 1500 (d). In case of different SiO$_2$/Al$_2$O$_3$ ratios as shown in FIG. 1D (a)-(d), ZSM-5 with silica to alumina ratio 80 and above showed highest mesostructure, while ZSM-5-23 showed less ordered hexagonal phase.

Overall, these results showed that formation of micro/meso composite varies and can remain unique based on ZSM-5 crystal size and on ZSM-5 SiO$_2$ to Al$_2$O$_3$ ratios.

FIGS. 2A-2F show effects of steaming. As mentioned above, steaming is the dealumination process and structural deformity or stability of a nanocarrier can be evaluated by the extent of structural retention after steaming. Steaming of zeolite tends to remove the framework aluminum and reduce the acidity of Bronsted acid sites.

Figure 2A:
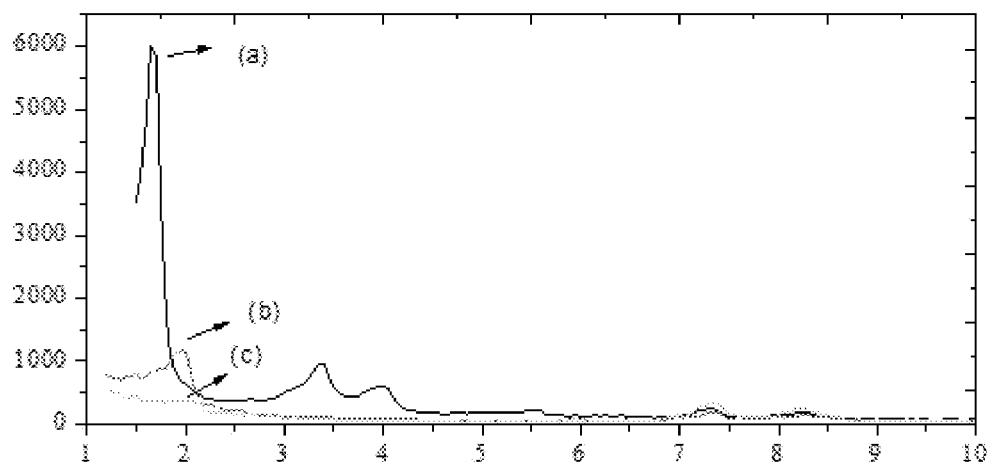
FIGS. 2A-2C show the XRD spectra of hierarchical ZSM-5 steamed samples ($SiO_2/Al_2O_3$=22-27) with different crystal sizes 2.0 μm (a), 0.5 μm (b) and 3.0 μm (c), respectively.
Figure 2B:
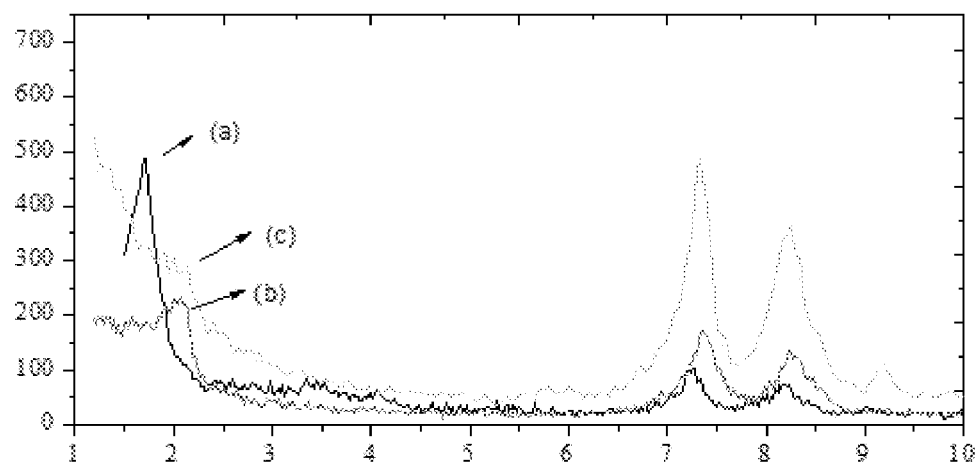
Figure 2C:
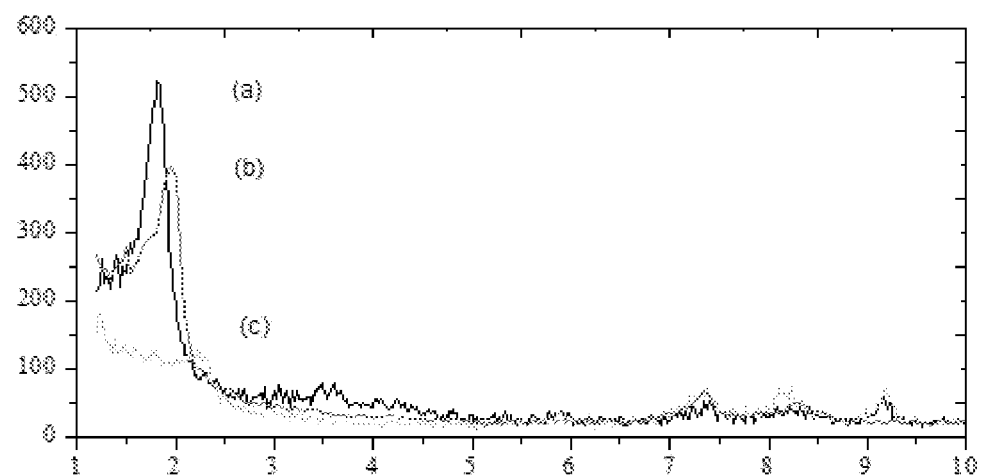

FIGS. 2A-2C show the steaming effect over hierarchical ZSM-5 of different crystal sizes. FIG. 2A corresponds to crystal size 2 µm, FIG. 2B corresponds to crystal size 0.5 µm and FIG. 2C corresponds to crystal size 3 µm.

Figure 2D:
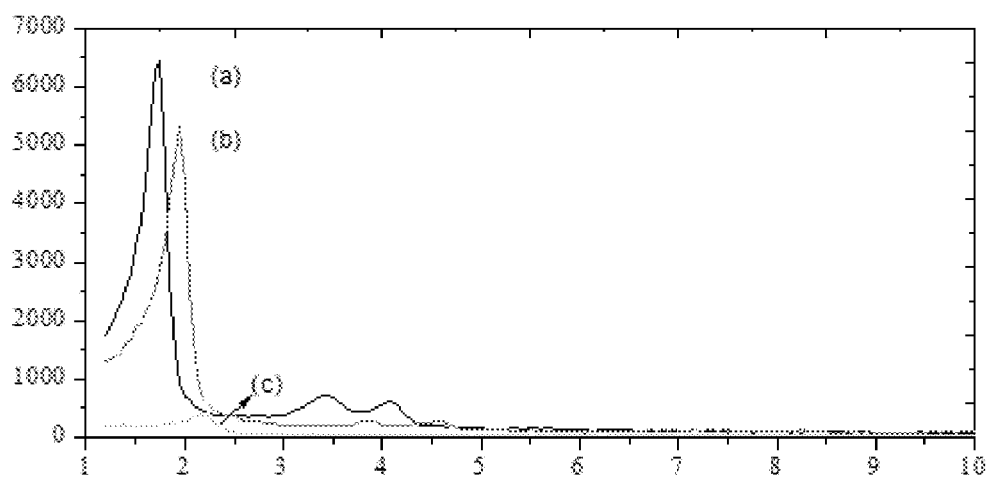
FIG. 2D-2F show the XRD spectra of hierarchical ZSM-5 steamed samples of different $SiO_2/Al_2O_3$ ratios (80, 280 and 1500, respectively) for micro/meso hierarchical formation with NaOH/CTAB ratio of 0.62.
Figure 2E:
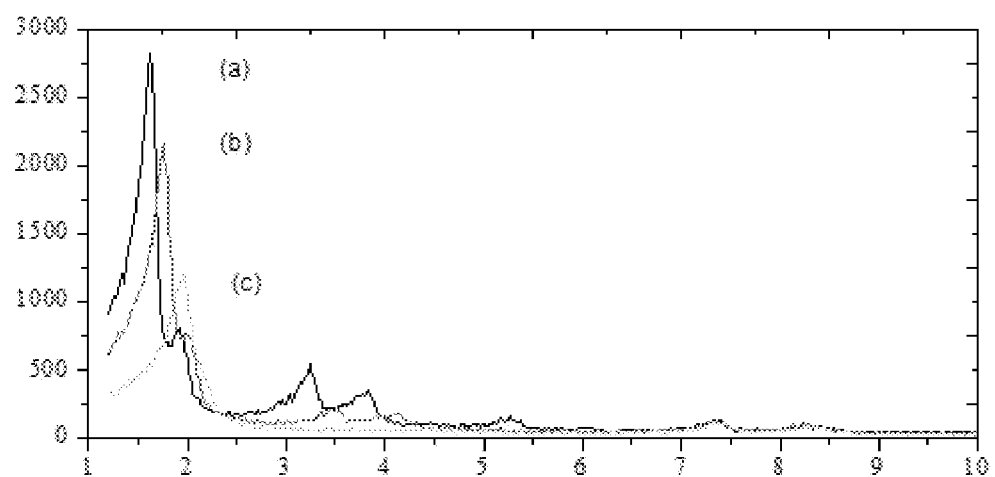
Figure 2F:
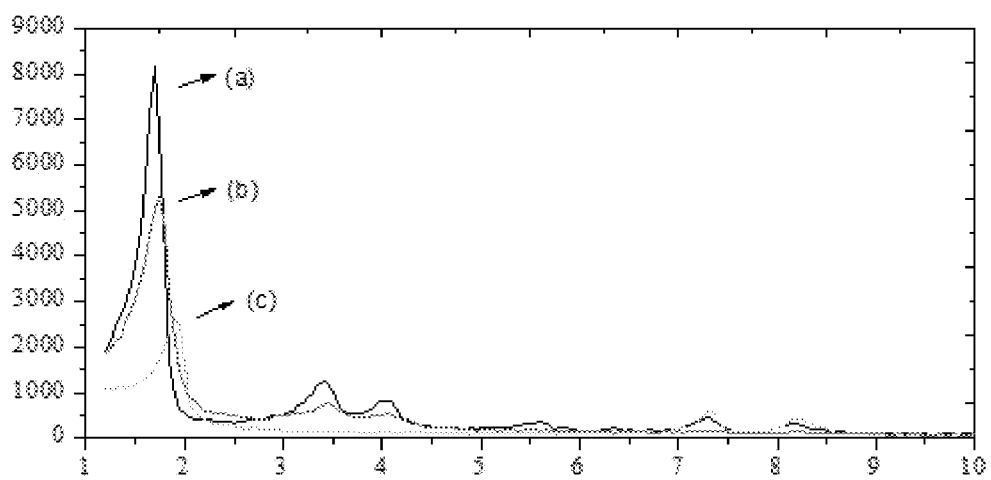

FIGS. 2D-2F show the steaming effect over hierarchical ZSM-5 of four different SiO$_2$ to Al$_2$O$_3$ ratios of 23, 80, 280 and 1500. FIG. 2D(a) corresponds to 80, FIG. 2D(b) to 280 and FIG. 2D(c) to 1500.

In case of ZSM-5-22, a highly intense hexagonal peak occurs with alkaline to template ratio of 0.62, FIG. 2A (a). However, an abrupt decrease in the hexagonal peak intensity at (100) plane was observed, while peak corresponding to (110 and 200) completely disappears at steaming temperature of 700° C., FIG. 2A (b). It can be observed even Bragg peak (100) completely disappear at 750° C., FIG. 2A(c). The textural analysis shows an apparent loss in the surface area from 500 m$^2$/g to 172 m$^2$/g, see Table 2.

TABLE 2

Textural characteristics of steamed ZSM-5 (SiO$_2$/Al$_2$O$_3$ = 22-23) with crystal sizes
(0.5 and 2.0 µm and SiO$_2$/Al$_2$O$_3$ ratios (23, 80, 280 and 1500) over NaOH/CTAB ratio 0.62.

| Sample | Steam temp (° C.) | SiO$_2$/Al$_2$O$_3$ ratio | NaOH/CTAB ratio | Surface area (m$^2$/g) multi | t-plot Micropore area (m$^2$/g) | Pore volume (cc/g) | t-plot Micropore volume (cc/g) | Mesopore volume (cc/g) | PD (nm) |
|---|---|---|---|---|---|---|---|---|---|
| ZSM-5 | 750 | 23 | — | 295 | 219 | 0.22 | 0.11 | 0.11 | — |
| ZSM-5 | 750 | 80 | — | 337 | 218 | 0.26 | 0.11 | 0.15 | — |
| ZSM-5 | 750 | 280 | — | 351 | 147 | 0.21 | 0.07 | 0.14 | — |
| ZSM-5 | — | 22 | 0.62 | 500 | — | 0.65 | — | 0.65 | 5.20 |
| ZSM-5 | 700 | 22 | 0.62 | 210 | 63 | 0.31 | 0.10 | 0.21 | 6.82 |
|  | 750 | 22 | 0.62 | 172 | 54 | 0.30 | 0.08 | 0.22 | 8.20 |
| ZSM-5 | — | 23 | 0.62 | 629 | — | 0.75 | — | 0.75 | 4.80 |
| ZSM-5 | 700 | 23 | 0.62 | 310 | 91 | 0.49 | 0.05 | 0.44 | 6.41 |
|  | 750 | 23 | 0.62 | 183 | 80 | 0.54 | 0.04 | 0.50 | 11.88 |
| ZSM-5 | — | 80 | 0.62 | 779 | 0 | 0.78 | — | 0.78 | 3.91 |
| ZSM-5 | 700 | 80 | 0.62 | 785 | — | 0.55 | — | 0.55 | 2.84 |
|  | 750 | 80 | 0.62 | 607 | — | 0.50 | — | 0.50 | 3.29 |
| ZSM-5 | — | 280 | 0.62 | 902 | — | 0.60 | — | 1.07 | 4.75 |
| ZSM-5 | 700 | 280 | 0.62 | 736 | — | 0.77 | — | 0.77 | 4.18 |
|  | 750 | 280 | 0.62 | 574 | — | 0.61 | — | 0.61 | 4.26 |
| ZSM-5 | — | 1500 | 0.62 | 710 | 0 | 0.58 | — | 0.58 | 3.28 |
| ZSM-5 | 700 | 1500 | 0.62 | 501 | 72 | 0.41 | 0.05 | 0.36 | 3.21 |
|  | 750 | 1500 | 0.62 | 494 | 11 | 0.49 | 0.01 | 0.48 | 3.98 |

Steaming effect showed the generation of micropore surface area, while a decrease was observed in the pore volume from 0.65 to 0.30 cc/g. The pore diameter increased from 5.2 nm to 8.2 nm.

Similar textural changes were observed over ZSM-5-23 (0.62), FIG. 2B (a)-(c).

Similar textural changes were also observed for ZSM-5-27 (0.62), FIG. 2C (a)-(c).

Comparatively, the diffraction pattern of ZSM-5-80 (0.62) showed steam stability at 700° C., FIG. 2D (a) and (b). The sample retained high surface area of 785 m$^2$/g, while a decrease in the mesopore volume and pore size distribution of about 30% was observed. Even at 750° C., the sample exhibited considerable retention of textural properties, FIG. 2D(c).

The steam stability trend increased further with high silica to alumina ratio 280 and 1,500, which showed impressive steam stability even at high temperature of 750° C., FIG. 2E (a)-(c). For instance, ZSM-5-280 (0.62) sample retained a surface area of 574 m$^2$/g at 750° C. The pore volume and pore size distributions showed no significant changes.

ZSM-5-1500 (0.62) showed a similar retention of a mesophase diffraction pattern and textural characteristics at such high steaming condition, FIG. 2F (a)-(c).

Figure 3A:
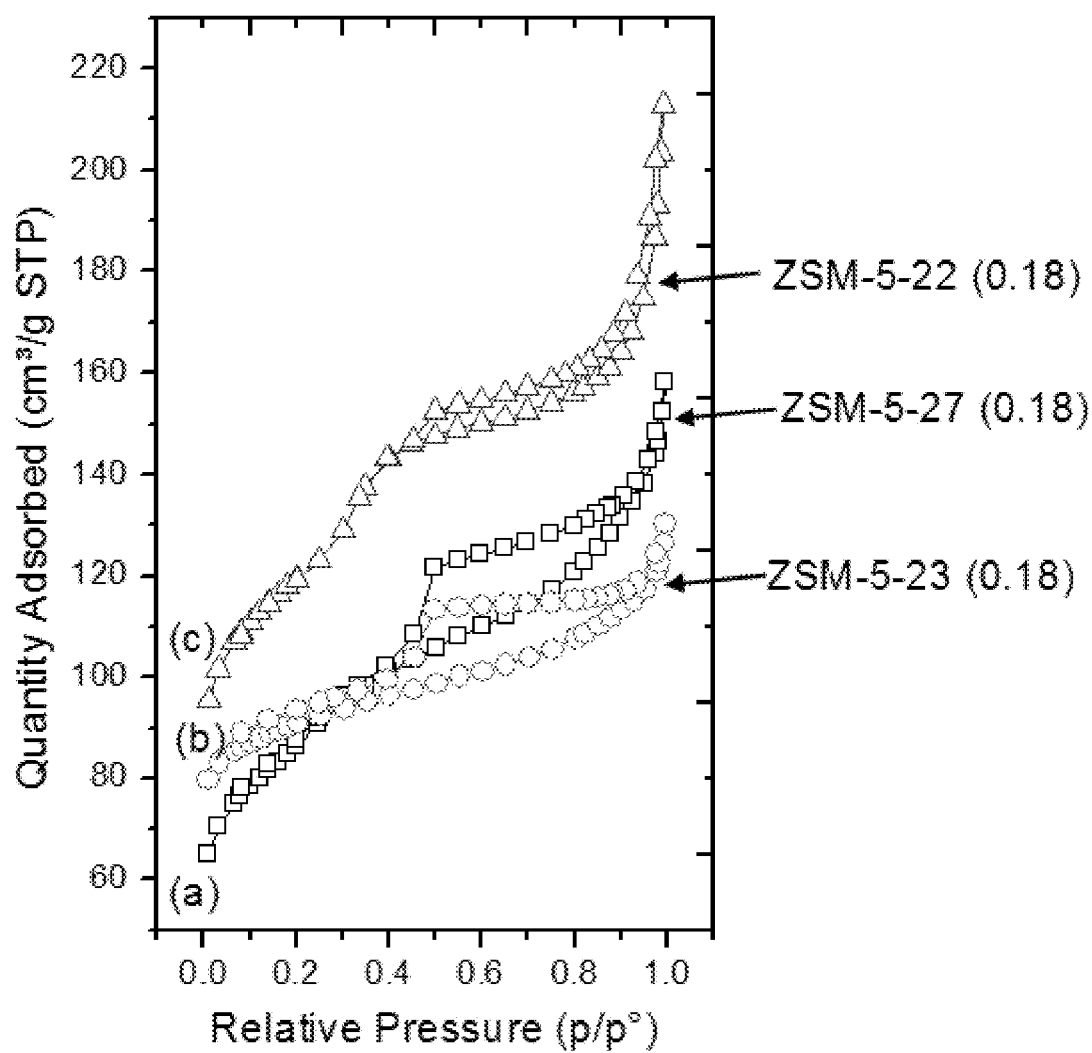
FIG. 3A shows $N_2$ adsorption isotherms of hierarchical composites of three different crystal sizes: 0.5 μm (b), 2.0 μm (c) and 3.0 μm (a) synthesized through top-down methodology.
Figure 3B:
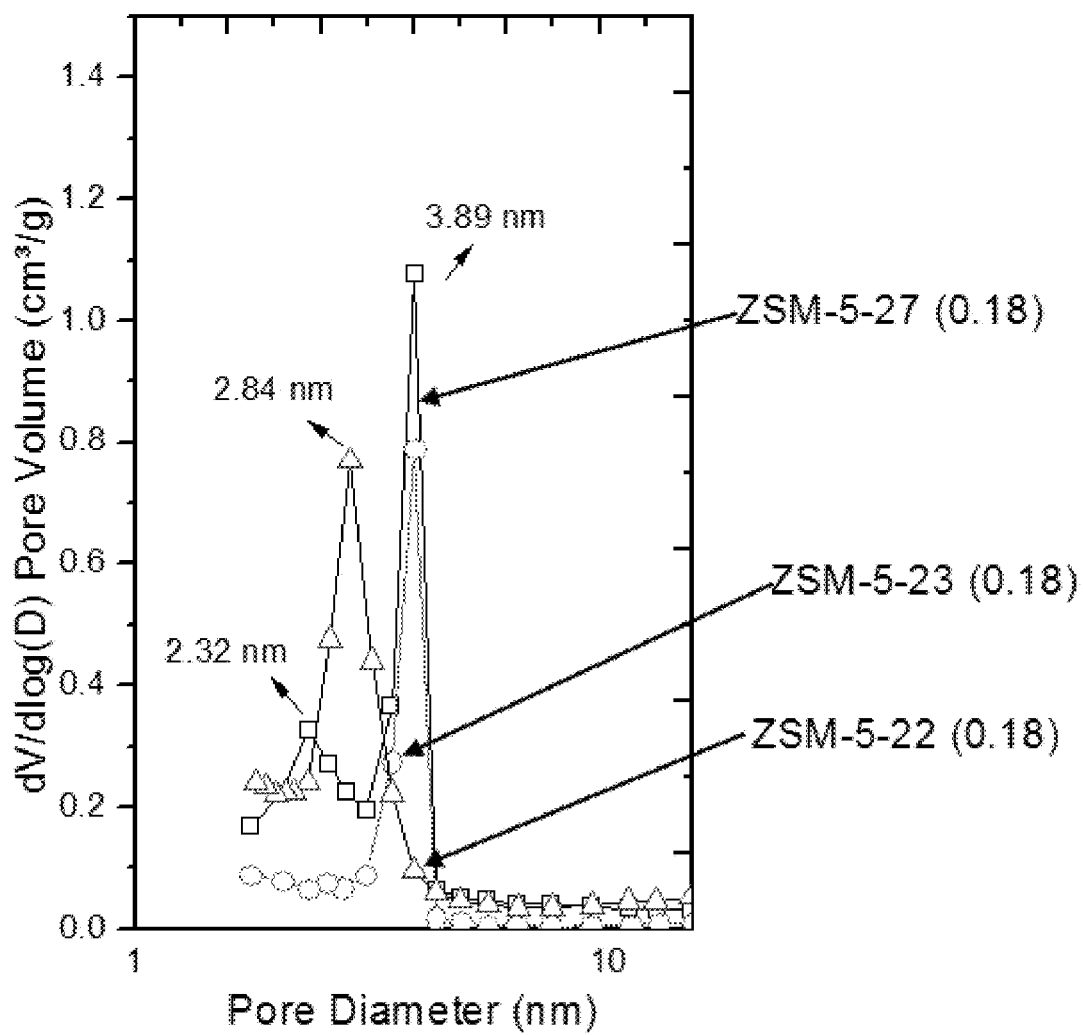
FIG. 3B shows pore size distributions of hierarchical composites of three different crystal sizes: 0.5 μm (b), 2.0 μm (c) and 3.0 μm (a) synthesized through top-down methodology.

FIG. 3 shows textural characteristics technique (N$_2$ adsorption isotherm and pore size distributions) of hierarchical composites based on ZSM-5 having three different crystal sizes 0.5 (b), 2.0 (c) and 3.0 µm (a) synthesized through top-down methodology. In this case, three samples were treated with alkaline to template ratio (NaOH/CTAB ratio of 0.18). The remaining synthesis steps such as pH adjustment and hydrothermal treatment was maintained constant. The adsorption isotherm pattern shows that in case of ZSM-5-22 (0.18) sample, an intermediate type IV and I isotherm was observed reciprocating a micro/meso hierarchical pore composite formation. A significant mesostructural reorganization at lower alkaline treatment ratio occurred with improvised surface area from 330 m$^2$/g to 388 m$^2$/g, while micropore characters remains intact without significant level changes from 205 m$^2$/g to 200 m$^2$/g. The pore volume showed a significant jump from 0.20 cc/g to 0.33 cc/g, where the mesopore volume enhanced from 0.08 to 0.23 cc/g. Most remarkably, pore size distribution study showed the presence of single and dual pore size distributions depending on the crystal size of ZSM-5.

In case of ZSM-5-22 (0.18), unimodal pores occur at 3.39 nm (Table 1). For ZSM-5-27 (0.18), a well distinguishable H4 hysteresis at p/p0~0.45 shows the presence of larger defective holes generated through alkali treatment top down approach. The presence of dual type of pores was observed at 2.32 nm and 3.89 nm, respectively. A slight increase in surface area was observed from 278 m$^2$/g to 289 m$^2$/g, while micropore surface clearly decreases from 170 m$^2$/g to 102 m$^2$/g. The total pore volume increase from 0.2 to 0.24 cc/g, in which the micropore contribution decreases significantly from 0.12 to 0.05 cc/g, respectively.

The alkaline treatment over nano ZSM-5-23 sample, showed a less vertical condensation step with unimodal pore system signaling reduced pore diameter and presence of increased microporous character compared to meso structure.

The textural analysis (Table 1) shows that the surface area of nano ZSM-5-23 was of 342 m$^2$/g, whereas micropore area constituted a major portion with surface area of 244 m$^2$/g.

At NaOH/CTAB ratio 0.18, the multipoint surface area remains almost unchanged at 347 m$^2$/g, while micropore surface reduced from 244 m$^2$/g to 198 m$^2$/g.

The micropore volume of ZSM-5-23 (0.18) reduced from 0.13 cc/g to 0.10 cc/g, indicating an overall variations in micropore surface area characteristics than mesopore with alkaline treatment ratio of 0.18.

However, with an alkaline to template ratio 0.62, textural characteristics with respect to ZSM-5-23 (0.62) were significantly changed. ZSM-5-23 (0.62) surface area was almost doubled, while ZSM-5-22 (0.62) showed an increase from 388 m$^2$/g to 500 m$^2$/g. The total pore volume and pore diameter of ZSM-5-23 (0.62) was found to be 0.75 cc/g and 4.80 nm, respectively.

The influence of alkaline to template ratios of 0.18 and 0.62 was studied over hierarchical ZSM-5-23, ZSM-5-80, ZSM-5-280, and ZSM-5-1500, respectively. The results showed that among different ratios, the samples ZSM-5-80 (0.18), ZSM-5-280 (0.18), ZSM-5-80 (0.62), and ZSM-5-280 (0.62) exhibited high mesoporous characteristics (Table 1).

The alkaline to template ratio tends to be critical in determining micro and mesophase. An increase of ratio from 0.18 to 0.62, showed a complete disappearance of micropore surface area (Table 1). For instance, ZSM-5-80 (0.62) showed the BET surface area of 779 m²/g with pore volume of 0.78 cc/g, respectively. However, $N_2$ adsorption is usually used to measure the mesopores rather than micropores. Due to increased physical adsorption in the case of micropore and need for certain relative pressure ($10^{-7}$-$10^{-5}$), it becomes difficult to analyze measure surface area accurately at pores less than 2 nm; J. Zhao, H. Xu, D. Tang, J. P. Mathews, S. Li, S. Tao, Fuel 183 (2016) 420-431. Overall, these results clearly indicate that the textural variations in micro and meso phase distributions among the hierarchical ZSM-5 with similar silica to alumina ratio but with different crystal sizes and ZSM-5 with different silica to alumina ratios over two different NaOH/CTAB ratio 0.18 and 0.62, respectively.

FIGS. 4A-4F show the $NH_3$-TPD acid site concentration and total acidity data profile of ZSM-5 with different crystal sizes 0.5, 2.0 and 3.0 μm and different $SiO_2/Al_2O_3$ ratios 23, 80, 280 and 1500. The total acidity is presented in Table 3. ZSM-5-27 has a crystal size of 3 μm, ZSM-5-22 has a crystal size of 2 μm and ZSM-5-23 has a crystal size of 0.5 μm. Methods for determining weak, medium or strong acid sites are known in the art and incorporated by reference to Rodriquez, et al., Applied Catalysis A: General Volume 328, Issue 2, 10 Sep. 2007, Pages 174-182.

CoQ10 coordinates strongly through the O—H . . . O═C linkage. Based on experimental studies it was determined that hydrogen bonding/electrostatic attraction was important for coordination. A top-down approach generated Lewis acid sites that coordinated with electron rich isoprene units of CoQ10.

Results show that ZSM-5 with similar silica to alumina ratios exhibits different strengths of acid sites.

Figure 4B:
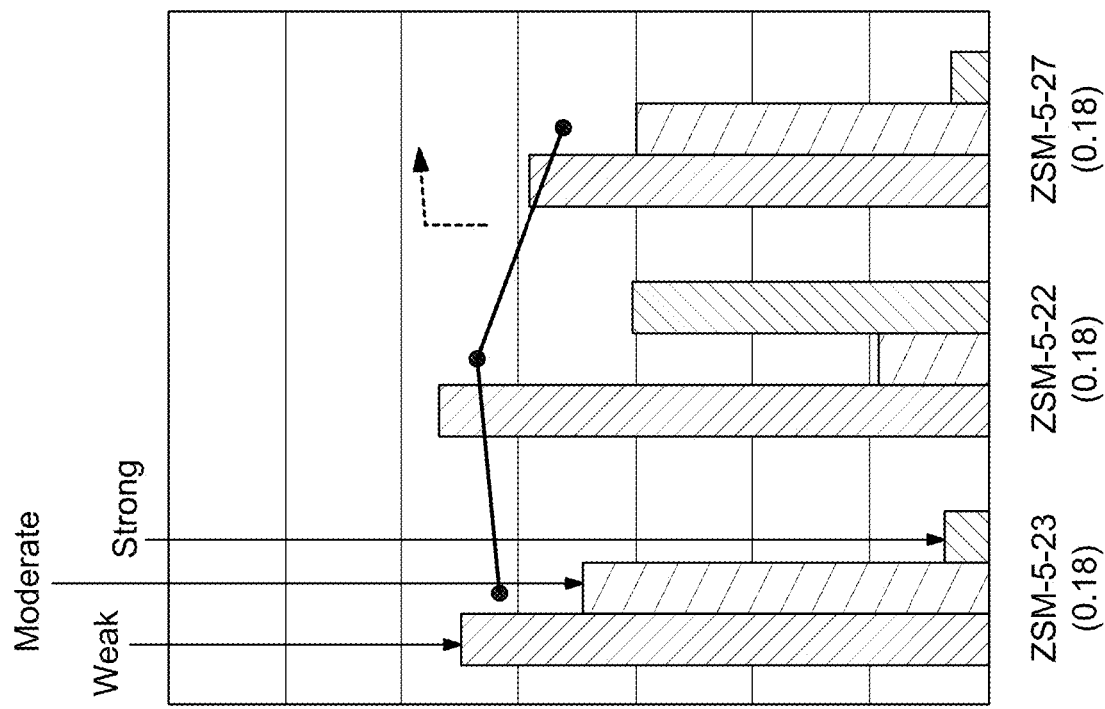
FIGS. 4A-4F show $NH_3$-TPD acidity data profiles of ZSM-5 with different crystal sizes 0.5 μm, 2.0 μm and 3.0 μm and different $SiO_2/Al_2O_3$ ratio 23, 80, 280 and 1500 respectively with NaOH/CTAB ratio of 0.18 and 0.62, respectively.
Figure 4A:
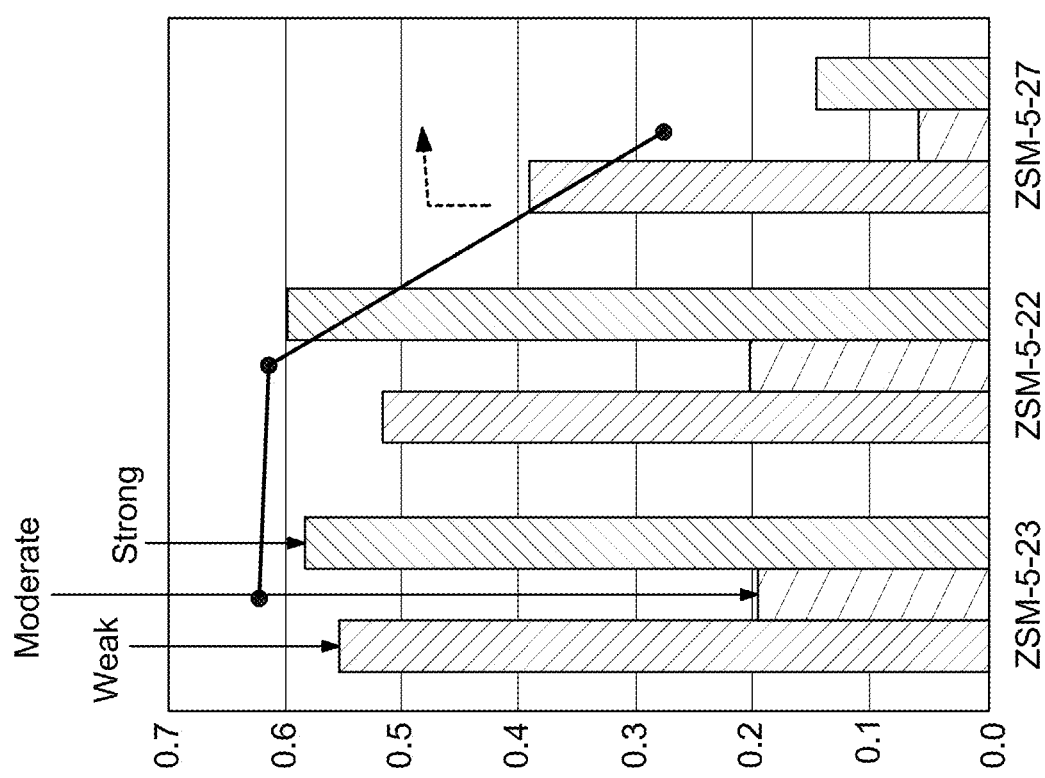

In case of parent ZSM-5 with ratio 22 and 23, a well-defined weak, medium and strong acid sites are present than ZSM-5 with ratio 27, see FIG. 4A.

The alkaline treatment with NaOH/CTAB ratio 0.18 tends to decrease the total acidity and strong acid sites. ZSM-5-23 (0.5 μm) and ZSM-5-22 (2 μm) showed the highest total acidity (1.334 and 1.313 mmol/g), while micron sized ZSM-5-27 showed lowest total acidity (0.596 mmol/g).

A significantly weak, medium and strong acid sites are found over ZSM-23 and ZSM-22 than ZSM-27, see FIG. 4A. It shows the disintegration features of ZSM-23 and ZSM-27 during alkaline treatment leading to extraction of silica and subsequent reassembly occurs in similar fashion.

The alkaline treatment with NaOH/CTAB ratio of 0.18 showed retention of weak and strong acid sites over ZSM-22, while considerable decrease in the strong acid sites are observed with ZSM-5 ratio 23, and ZSM-5-27, respectively, FIG. 4B. Increasing the NaOH/CTAB ratio to 0.62 further decreases the total acidity including weak, medium and strong acid sites over ZSM-5-27 than ZSM-5-23 and ZSM-5-22, see FIG. 4C.

Figure 4D:
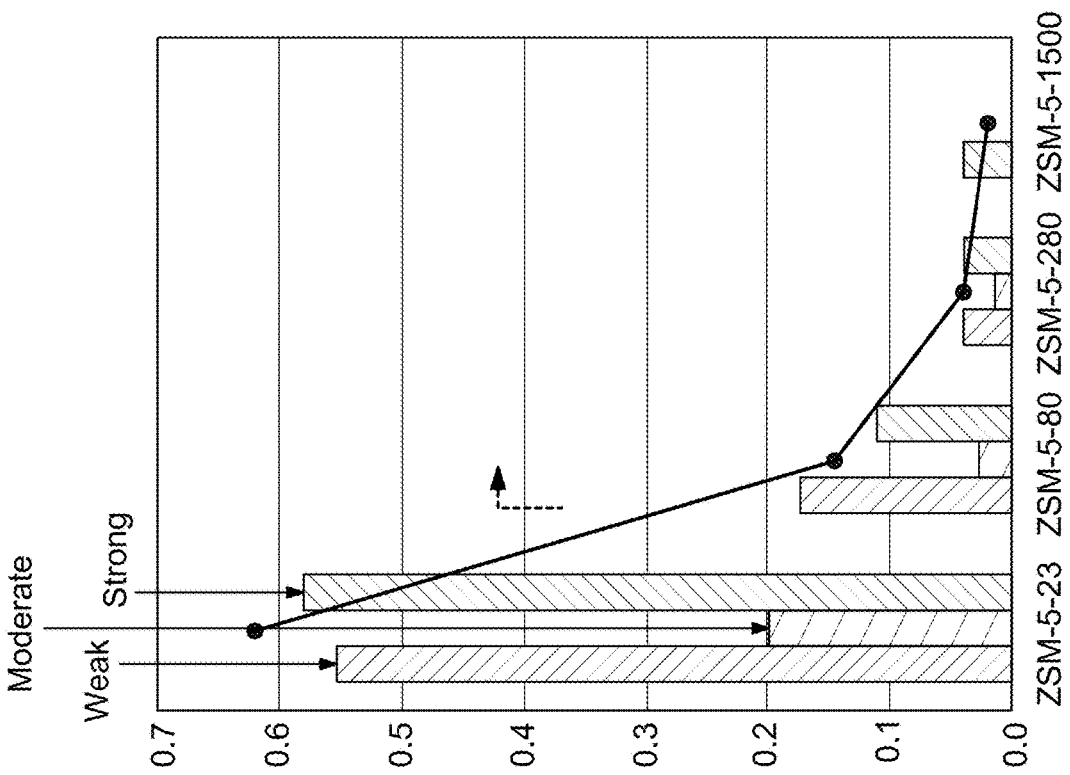
Figure 4C:
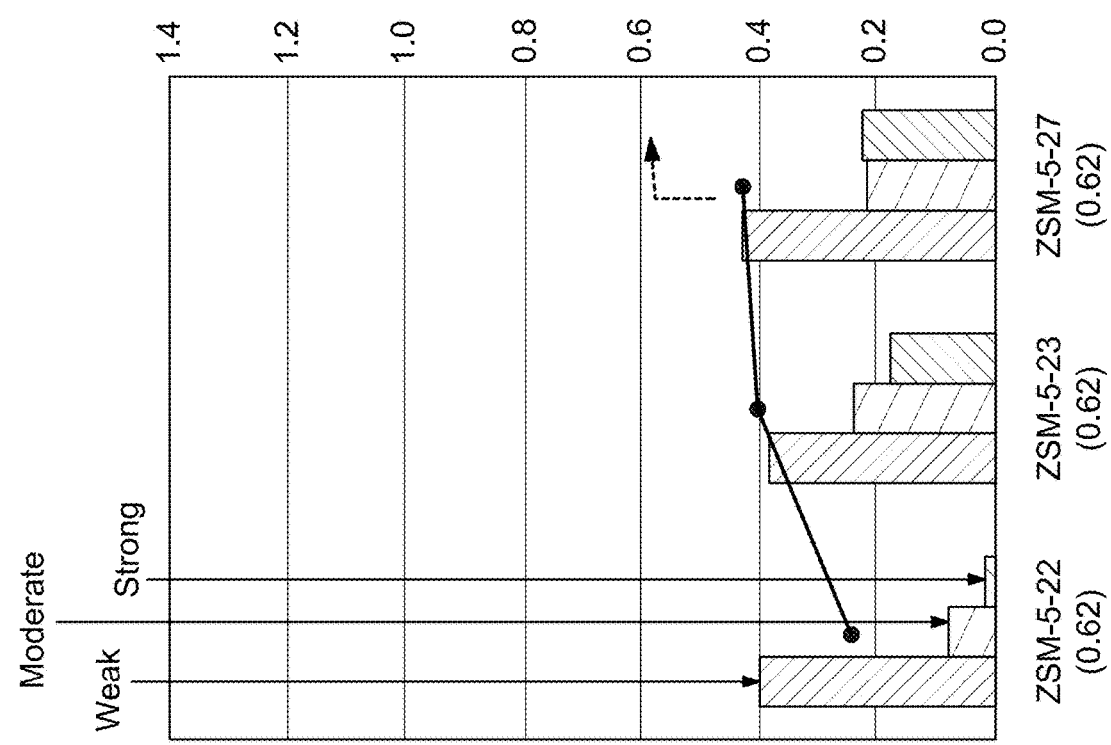
Figure 4E:
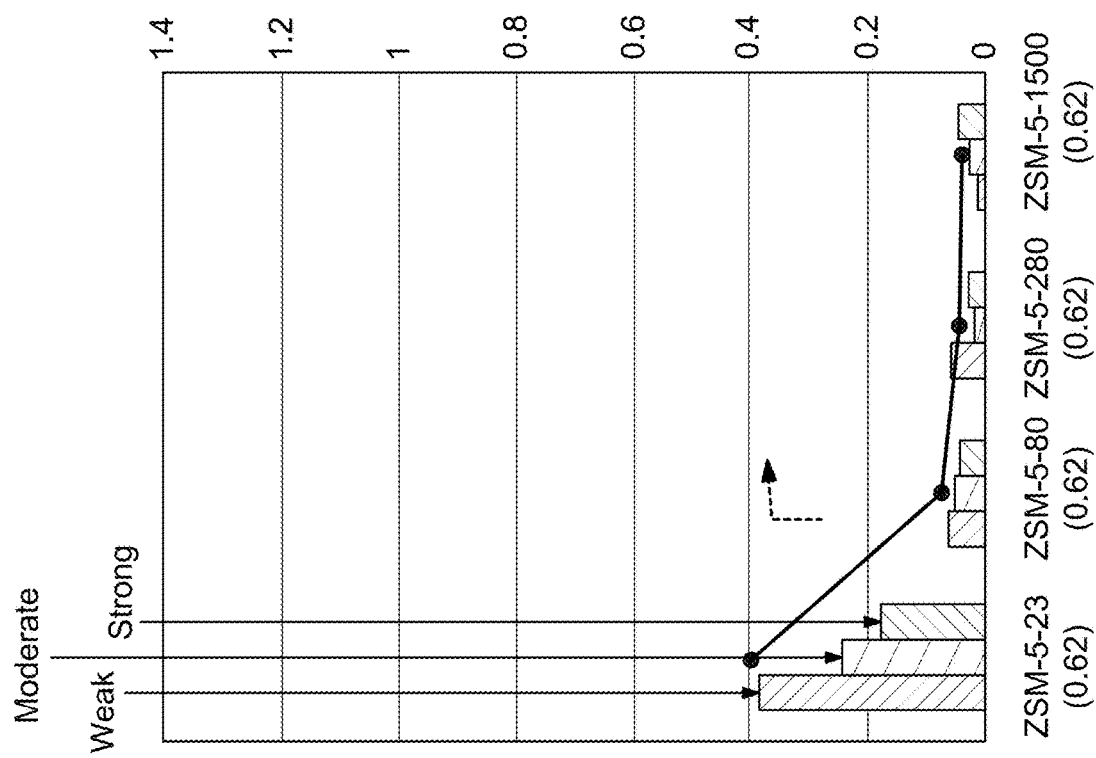
Figure 4F:
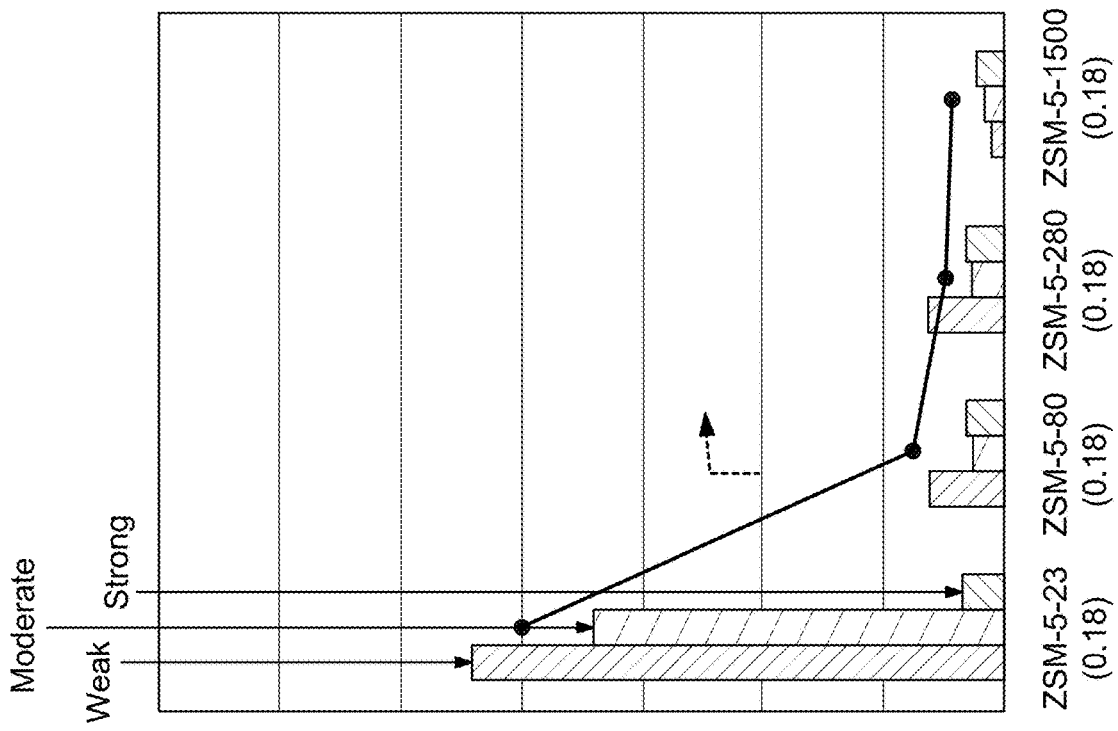

The acidity profile was analyzed for ZSM-5 and hierarchical ZSM-5 of different ratios, FIGS. 4D-4F. Parent ZSM-5 23, 80, 280, and 1500 exhibit a typical acid site distribution profile, where ZSM-5-23 showed high total acidity of 1.334 mmol/g, while ZSM-5-80, ZSM-5-280 and ZSM-5-1500 showed a subsequent reduced total acidity of 0.309, 0.083 and 0.040 mmol/g, respectively.

Treatment with alkaline to template ratio 0.18, the total acidity and peak intensity corresponding to weak, moderate

TABLE 3

$NH_3$-TPD acid site concentration and total acidity of ZSM-5 with different crystal sizes (0.5, 2.0 and 3.0 μm) and different $SiO_2/Al_2O_3$ ratios 23, 80, 280 and 1500.

| Sample | $SiO_2/Al_2O_3$ ratio | NaOH/CTAB ratio | Weak (100-250° C.) | Medium (250-350° C.) | Strong (350-550° C.) | Total acidity (mmol/g) |
|---|---|---|---|---|---|---|
| ZSM-5-22 (2 μm) | 22 | — | 0.515 | 0.201 | 0.597 | 1.313 |
| ZSM-5-23 (0.5 μm) | 23 | — | 0.554 | 0.198 | 0.582 | 1.334 |
| ZSM-5-27 (3 μm) | 27 | — | 0.391 | 0.059 | 0.146 | 0.596 |
| ZSM-5-22 | 22 | 0.18 | 0.460 | 0.090 | 0.304 | 0.854 |
| ZSM-5-23 | 23 | 0.18 | 0.441 | 0.341 | 0.036 | 0.818 |
| ZSM-5-27 | 27 | 0.18 | 0.385 | 0.300 | 0.031 | 0.716 |
| ZSM-5-22 | 22 | 0.62 | 0.200 | 0.038 | 0.006 | 0.244 |
| ZSM-5-23 | 23 | 0.62 | 0.190 | 0.120 | 0.088 | 0.398 |
| ZSM-5-27 | 27 | 0.62 | 0.367 | 0.109 | 0.112 | 0.588 |
| ZSM-5 | 23 | 0.18 | 0.441 | 0.341 | 0.036 | 0.818 |
| ZSM-5 | 80 | 0.62 | 0.032 | 0.023 | 0.020 | 0.075 |
| ZSM-5 | 280 | 0.18 | 0.060 | 0.024 | 0.027 | 0.111 |
| ZSM-5 | 1500 | 0.18 | 0.008 | 0.014 | 0.020 | 0.042 |
| ZSM-5 | 23 | 0.62 | 0.190 | 0.120 | 0.088 | 0.398 |
| ZSM-5 | 80 | 0.62 | 0.032 | 0.023 | 0.020 | 0.075 |
| ZSM-5 | 280 | 0.62 | 0.023 | 0.009 | 0.015 | 0.047 |
| ZSM-5 | 1500 | 0.62 | 0.008 | 0.014 | 0.020 | 0.042 |

In some embodiments, a hierarchical aluminosilicate of the invention will have 15, 20, 25, 30, 35, 40, 45, 50, 55, 60, 65 or 70% weak acid sites compared to its total acidity (weak, moderate and strong acid sites).

The weak acid sites are considered to fall between 100-250° C., moderate acid sites between >250-350° C. and strong acid sites between >350-550° C., as determined by $NH_3$-temperature programmed desorption (TPD) analysis.

and strong acid sites decreases with increased $SiO_2/Al_2O_3$ ratio (FIG. 4D). [Tom—did you provide ranges and sub ranges for the total acidity?]

In particular, hierarchical ZSM-5-80 showed a significant shift to weak acid sites, irrespective of alkaline treatment ratio of 0.18 and 0.62; FIGS. 4E and 4F. The acidity analysis substantiates that acidity property of ZSM-5 crystal sizes and ZSM-5 of different silica to alumina ratios can be adjusted through alkaline treatment ratio, where generation of nanozeolitic species in the mesostructural framework of the ZSM-5-80, ZSM-5-280 and ZSM-5-1500 induces weak acid sites.

Figure 5A:
FIGS. 5A-5C show the SEM images of parent ZSM-5-27, ZSM-5-23 and ZSM-5-280, respectively.
Figure 5B:
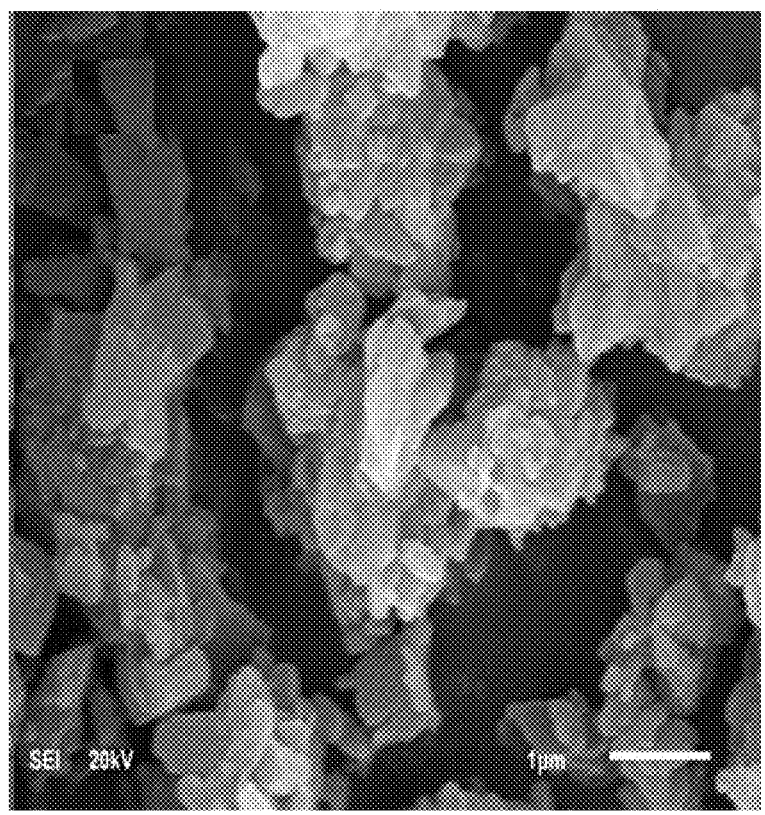
Figure 5C:
Figure 5D:
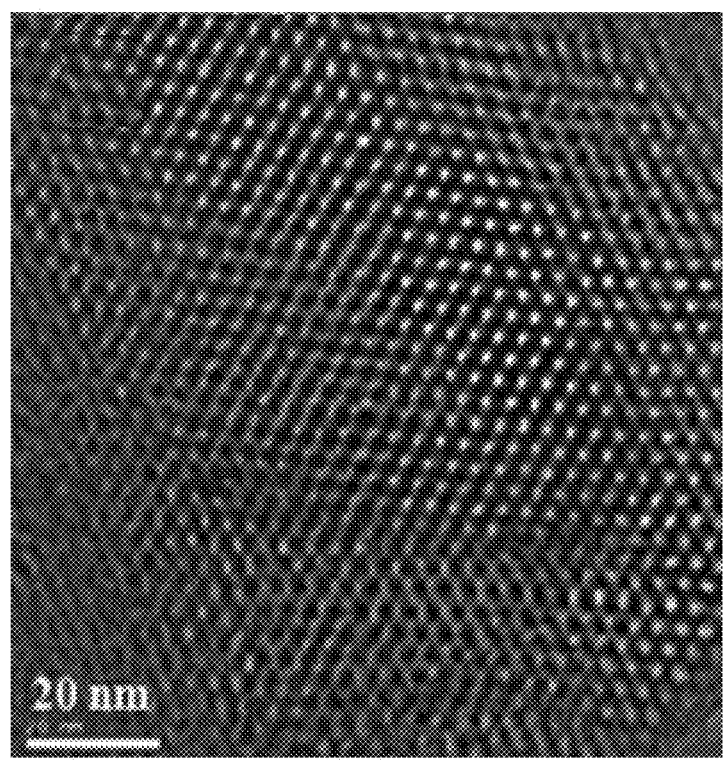
FIGS. 5D-5F show the TEM images with respect to AlMCM-41 and ZSM-5-27 (0.18) and ZSM-5-80 (0.62), respectively.
Figure 5E:
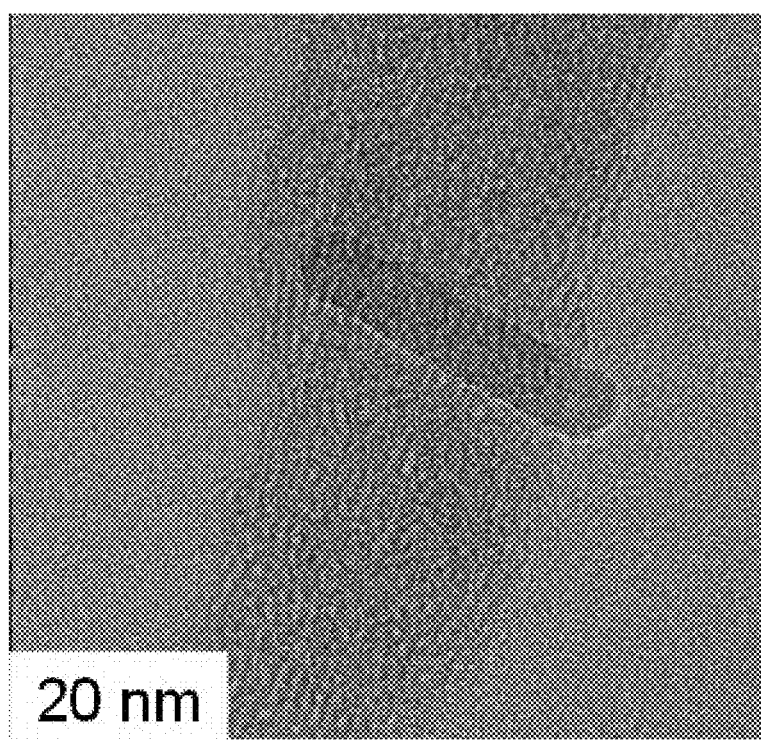
Figure 5F:
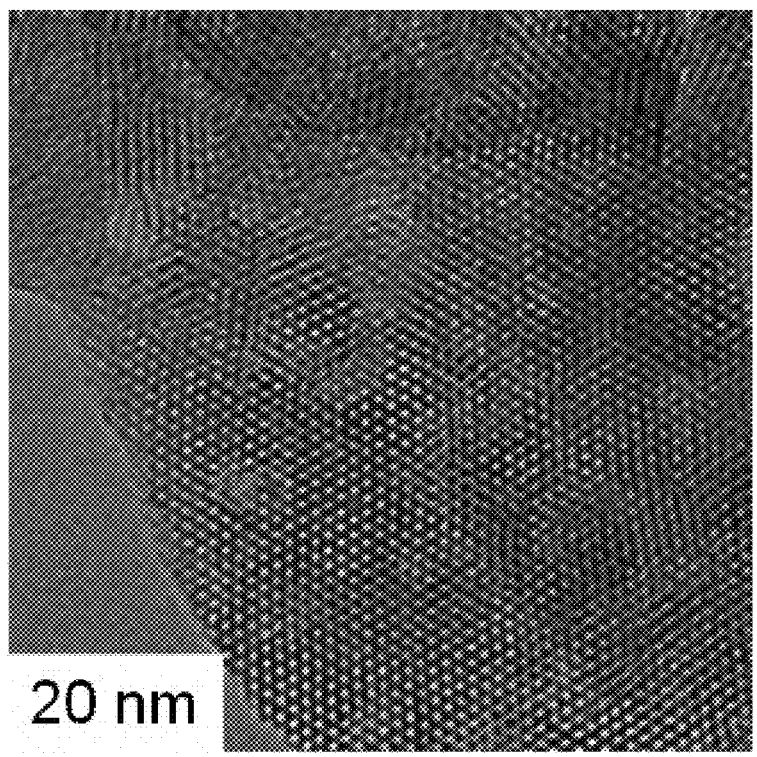

FIGS. 5A-5F shows the SEM images of parent ZSM-5-27, ZSM-5-23 and ZSM-5-280, and TEM images of AlMCM-41, ZSM-5-27 (0.18), and ZSM-5-80 (0.62), respectively. ZSM-5-27 shows the presence of bulk ZSM-5 crystal aggregates with mean size of 3.0 μm, while ZSM-5-23 showed the presence of irregular nanosized crystal in the range of 500 nm (0.5 μm). ZSM-5-280 showed the presence of bulk crystals of 2.4 μm (FIGS. 5A-5C). The nano pore ordering of AlMCM-41, ZSM-5-27 (0.18), and ZSM-5-80 (0.62) composite analyzed with TEM shows an controlled variation of micro and mesophase. In case of AlMCM-41, unperturbed hexagonal pore ordering was observed (FIG. 5D). In case of ZSM-5-27 (0.18), the mild alkaline treatment tends to retain ZSM-5 crystals in perpendicular direction of mesopore channels (FIG. 5E). In case of ZSM-5-80 (0.62), the NaOH/CTAB ratio to 0.62, shows the hexagonal pores, but unlike conventional MCM-41, presence of disordered phase was clearly observed, which are attributed to the nanozeolitic layers interlinked with the MCM-41 mesophase (FIG. 5F).

Adsorption of antioxidants: Influence of External Surface area. The external surface area is an important feature that affects the sorbent adsorption capability. A high surface area, exposes and makes available a large fraction of active sites able that results in higher adsorption of molecules; K. Heister. *How accessible is the specific surface area of minerals? A comparative study with Al-containing minerals as model substances*. Geoderma, 263 (2016) 8-15. In addition, extra framework aluminum in the zeolitic framework is reported have a greater influence on the sorption properties; G. D. Pringruber, P. Raybaud, Y. Belmabkhout, J. Cejka, A. Zukal, Phys. Chem. Chem. Phys. 12 (2010) 13534-13546. Therefore the influence of hierarchical aluminosilicate prepared through alkali treatment of ZSM-5-80, steaming and surface functionalization effect was studied. FIG. 6 shows the influence of external surface area on the adsorption of CoQ10.

Table 1 shows the textural characteristic feature of modified ZSM-5 samples. Parent ZSM-5-80 showed the lowest external surface area of 170 m$^2$/g, while hierarchical ZSM-5-80 (0.62) and steamed hierarchical ZSM-5-80 showed the highest external surface area of 843 m$^2$/g and 824 m$^2$/g, respectively. Steamed parent ZSM-5-80 (117 m$^2$/g) and functionalized samples ZSM-5-80 (0.62) S1, ZSM-5-80 (0.62) S2 and ZSM-5-80 (0.62) S3 showed the lowest external surface of 115 m$^2$/g, 134 m$^2$/g and 177 m$^2$/g, respectively. In case of ZSM-5-80 (0.18) treated with less alkaline condition of NaOH/CTAB ratio 0.18, showed less external surface area of 222 m$^2$/g. The dominance of external mesopore surface area occurs with increasing the ratio to 0.62. Comparatively, ZSM-5-80 (0.62) showed the highest contribution from mesopore surface and pore volume and pore diameter (Table 1). The high adsorption capacity of CoQ10 over ZSM-5-80 (0.62) indicates the importance of external mesopores dominance. Further, in order to show the importance for hierarchical aluminosilicate external surface effect, surface functionalization was carried out using three different types of silane groups such as 3-aminopropyltriethoxysilane, tetraethylenetetramine, and N-[-3-trimethoxysilyl)propyl]aniline silane over ZSM-5-80 (0.62). The external surface area reduced abruptly from 843 m$^2$/g of ZSM-5-80 (0.62), to 114 m$^2$/g, 134 m$^2$/g and 177 m$^2$/g, respectively. The reduction of 86%, 84% and 79% was found in all the three samples. Subsequently, the adsorption of Q10 over three samples was reduced to 19.2%, 34% and 37%, respectively. This shows the important aspect of external surface area of ZSM-5-80 (0.62) for adsorption activity.

Figure 7:
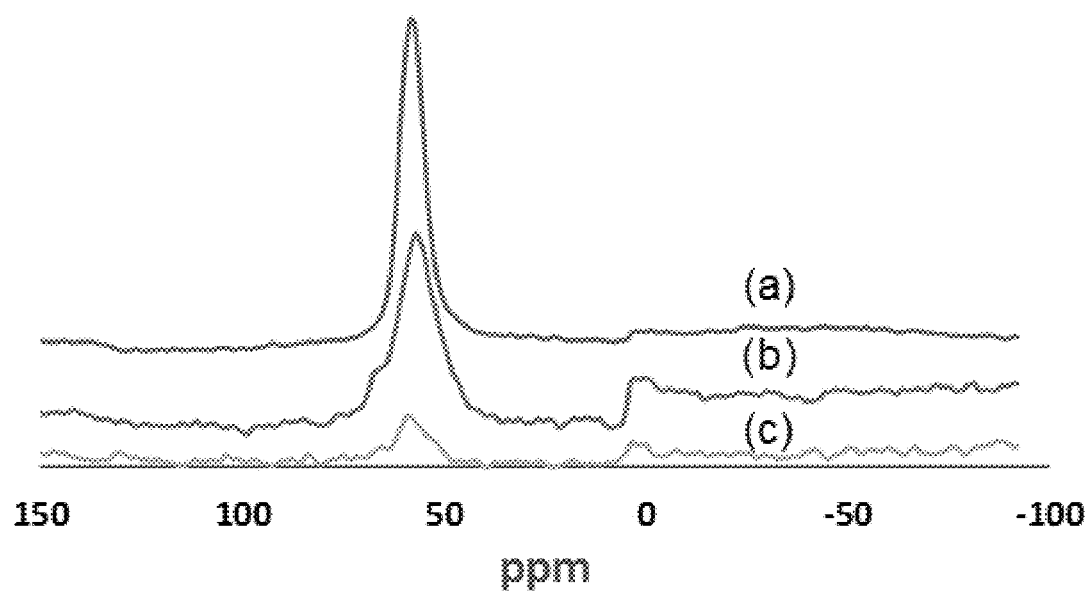
FIG. 7. $^{27}Al$ MAS NMR spectra of (a) parent ZSM-5-80, (b) pure amorphous AlMCM-41 and (c) hierarchical ZSM-5-80 (0.62) prepared through top-down approach.

$^{27}$Al MAS NMR spectroscopy. In order to study the active site responsible for CoQ10 adsorption, low adsorption support parent ZSM-5-80 and high adsorption support ZSM-5-80 (0.62) was chosen for further study. The local coordination nature of SiO$_2$ and Al$_2$O$_4$ tetrahedra of parent ZSM-5-80, pure amorphous AlMCM-41 and hierarchical ZSM-5-80 (0.62) prepared through top-down approach was investigated using $^{27}$Al MAS NMR (FIG. 7). Parent ZSM-5-80 showed presence of an intense single peak at about 58 ppm, indicating presence of exclusively framework coordinated tetrahedra Al species; S. H. Li, S. J. Huang, W. L. Shen, H. L. Zhang, H. J. Fang, A. M. Zheng, S. B. Liu, F. Deng, *Probing the spatial proximities among acid sites in dealuminated H-Y zeolite by solid-state NMR spectroscopy*. J Phys Chem C 112 (2008) 14486-14494.

In the case of parent amorphous framework constituted AlMCM-41, intense four coordinated Al species was observed but an additional peak appears at about 0 ppm, indicating the presence of six coordinated Al present as extra framework species. In case of hierarchical ZSM-5-80 (0.62), the signal corresponding to the tetrahedral Al species decreases significantly and coexisting of four and six coordinated extra framework aluminum species are observed with alkaline treatment of top-down methodology. The adsorption of CoQ10 capacity increased remarkably with increased external surface area from 170 m$^2$/g of ZSM-5-80 to 844 m$^2$/g of ZSM-5-80 (0.62) through top-down approach methodology, which indicates the dependency of adsorption over hierarchical BET external surface area, while generation of weak acid sites are important requirements rather than lower surface area and strong acid sites of ZSM-5-80. These data show synergism between balanced acid sites and external surface area for increased CoQ10 adsorption in coordination with hydrogen bonding and electrostatic attraction through strong and weak acid sites.

Figure 8A:
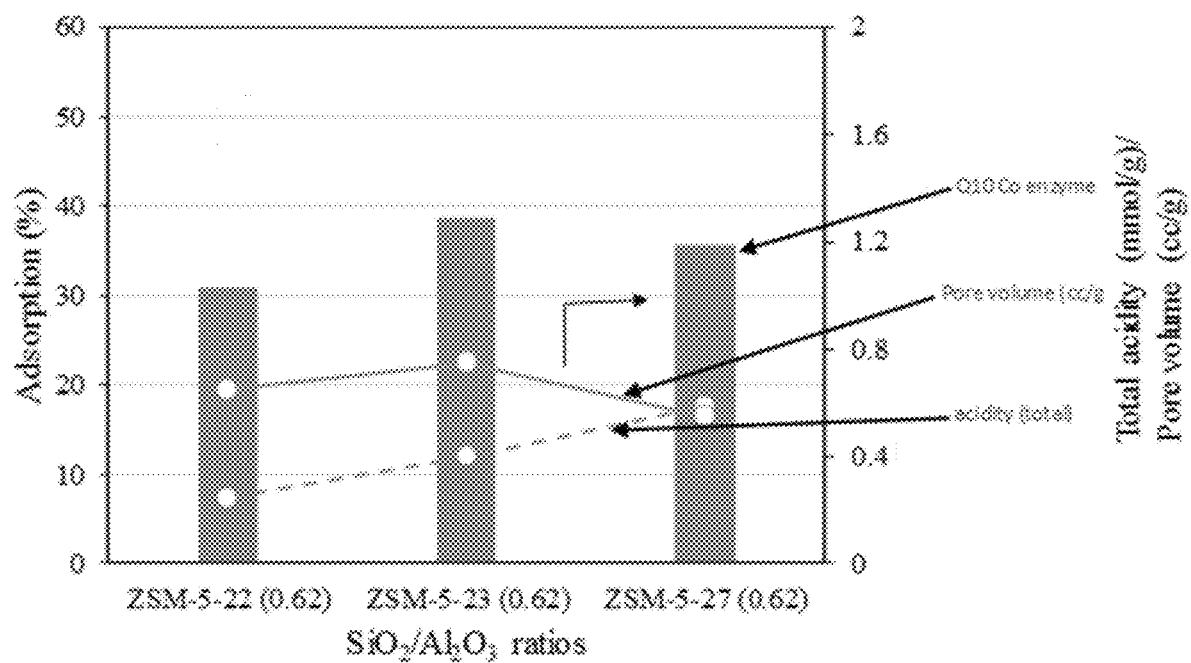
FIG. 8A. Effect on pore volume and total acidity on the adsorption of Q10 coenzyme (100 ppm) for 24 h of hierarchical ZSM-5 nanosupports produced from parent ZSM-5 having different crystal sizes. ZSM-5-23, ZSM-5-22 and ZSM-5-27, respectively, have crystal sizes of 0.5, 2, and 3 μm.
Figure 8B:
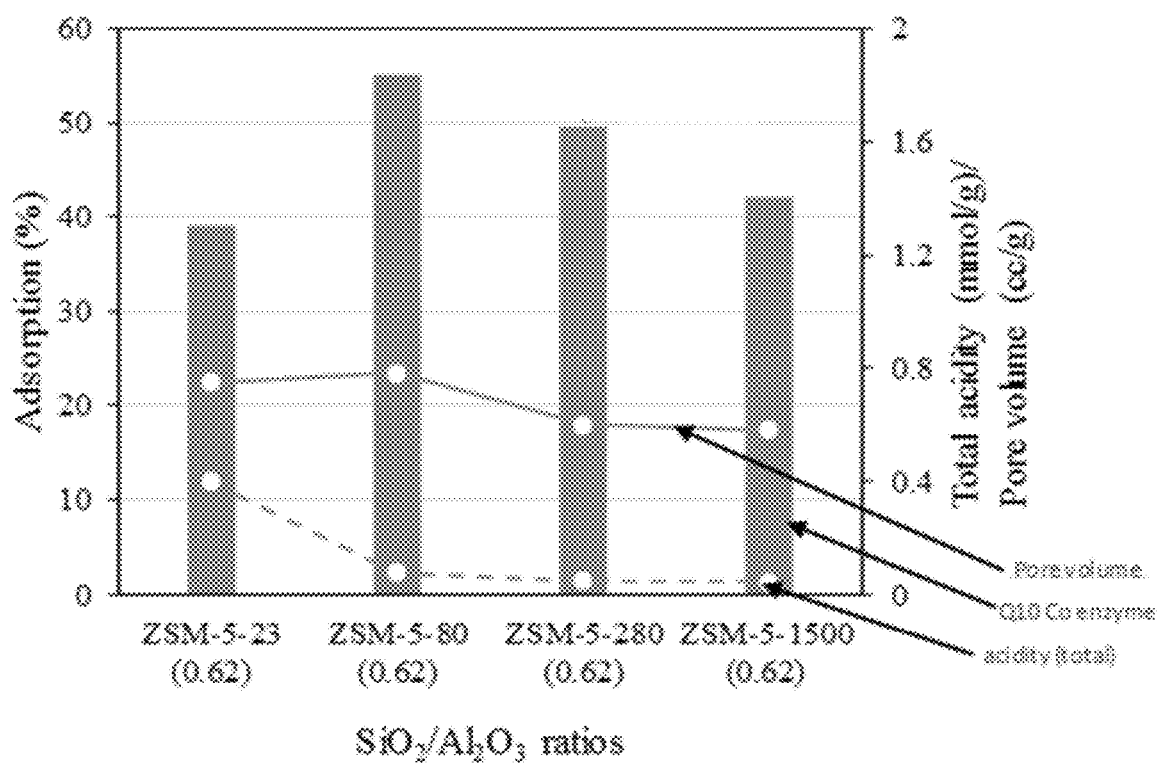
FIG. 8B. Effect on pore volume and total acidity on the adsorption of Q10 coenzyme (100 ppm) for 24 h of hierarchical ZSM-5 nanosupports produced from parent ZSM-5 having $SiO_2$ to $Al_2O_3$ ratios of 23, 80, 280 or 1500. ZSM-5-23, ZSM-5-80, ZSM-5-280 and ZSM-5-1500, respectively, have $SiO2/Al_2O_3$ ratios of 23, 80, 280 and 1500.

Influence of ZSM-5 silica to alumina ratios, acidity and pore volume. FIG. 8 shows the effect of hierarchical ZSM-5 (silica to alumina ratios 22-27) with different crystal sizes, and effect of different SiO$_2$ to Al$_2$O$_3$ ratio (23-1500), pore volume and total acidity on the adsorption of Q10 coenzyme at concentration of 100 ppm. Q10 coenzyme adsorption were found as following: Among the different crystal sized aluminosilicate materials, ZSM-5-23 (0.62) had the highest adsorption (39%), followed by ZSM-5-27 (0.62) (36%) and ZSM-5-22 (31%), respectively. Among the different silica to alumina ratios, ZSM-5-80 (0.62) had the highest adsorption (55%), followed by ZSM-5-280 (0.62) (49.5%), and ZSM-5-1500 (0.62) (42.1%), respectively. The study shows that adsorption over ZSM-5-23 (0.62) was highest among different crystal sizes, while with various silica to alumina ratios, ZSM-5-80 (0.62) was found to be best hierarchical ZSM-5 based support among all the tested zeolites. The reason for high adsorption capability was investigated through two different characterization techniques involving BET and TPD analysis. The study shows that as expected total acidity was highest at lower silica to alumina ratios 22-27, while interestingly hierarchical ZSM-5-80 to ZSM-5-1500 showed presence of less acidity most significantly weak acid sites. For instance, the weak, medium and strong acid sites of ZSM-5-23 (0.62) were of 0.190, 0.120 and 0.088 mmol/g, respectively. When textural characteristics of ZSM-5-80 (0.62) were compared, presence of weak acid sites is observed. The presence of weak, medium and strong acid sites was of 0.032, 0.023 and 0.020 mmol/g, respectively (Table 3). The adsorption study showed the necessity of weak acid sites with total acidity of 0.075 mmol/g of ZSM-5-80 (0.62) rather than of ZSM-5-23 (0.62) with high total acidity of 0.398 mmol/g. ZSM-5-280 (0.62) and ZSM-5-1500 (0.62) with lower total acidity of 0.047 and 0.042 mmol/g showed decreased adsorption, which indicates the necessity for optimum silica to alumina ratio for a balanced textural characteristics involving weak acidity. The pore volume was reported to be another important parameter for high adsorption process. The pore volume of 0.78 cc/g was found to be highest for ZSM-5-80 (0.62). Overall, mild acidity in conjugation with pore volume of hierarchical ZSM-5 was found to be critical for Q10 adsorption. Even with similar pore volume and total acidity of ZM1500 showed reduced adsorption, signaling importance of silica to alumina ratio. The study showed that highest Q10 adsorption observed in the pore volume range between 0.5-0.88 cc/g, while large pore volume slightly reduced the Q10 adsorption.

Figure 9:
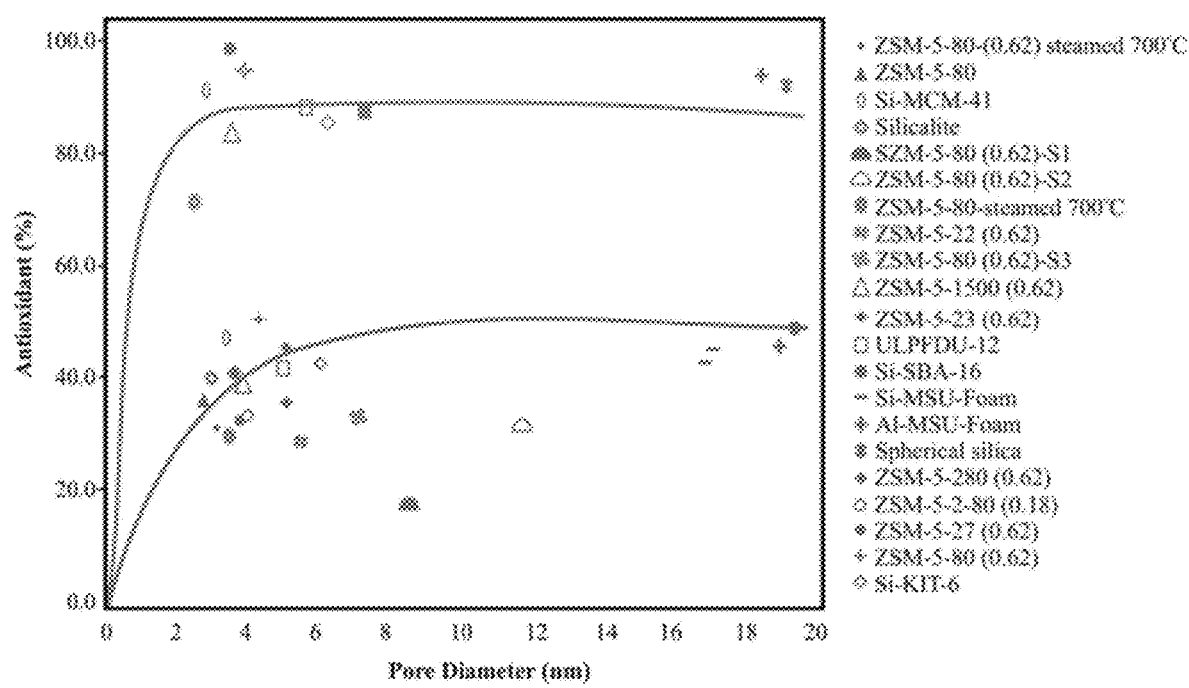
FIG. 9. Adsorption of curcumin (top graph) or CoQ10 (bottom graph) plotted against pore diameter of different structured nanocarriers. Symbols grouped around top graph denote nanocarriers used to adsorb curcumin and those grouped around bottom graph denote carriers used to adsorb CoQ10 (except for the top symbol "–" near the end of the lower graph which refers to Si-MSU-foam loaded with curcumin).
Figure 10A:
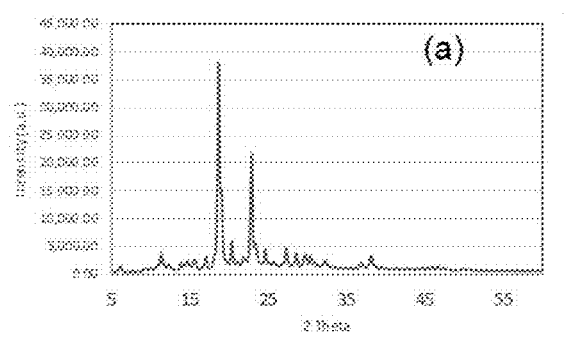
FIGS. 10A-10D show the XRD diffraction spectra of CoQ10, ZSM-5-80 (0.62), ZSM-5-80 (0.62)-S1 and ZSM-5-80 (0.62)-S2, respectively.
Figure 10B:
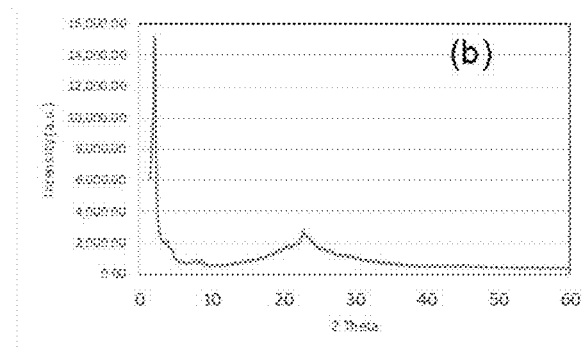
Figure 10C:
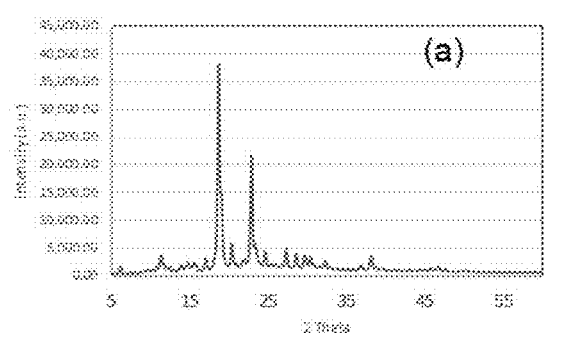
Figure 10D:
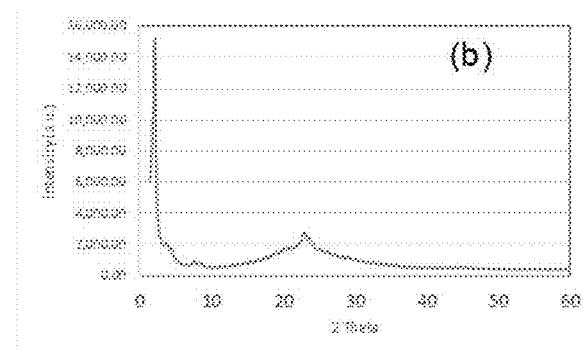

Influence of pore diameter of aluminosilicalites and structured silicas. The influence of pore diameter of aluminosilicates and several structured silicas is shown in FIG. 9. Parent ZSM-5-22, ZSM-5-23, ZSM-5-27, ZSM-5-80, ZSM-5-280, ZSM-5-1500, hierarchical ZSM-5 with different crystal sizes treated with NaOH/CTAB ratio 0.18 (ZSM-5 (0.18), ZSM-5-23 (0.18) and ZSM-5-27 (0.18) with pore diameter of 3.39, 2.87 and 3.38 nm) and treated with NaOH/CTAB ratio of 0.62 (ZSM-5-22 (0.62), ZSM-5-23 (0.62) and ZSM-5-27 (0.62) with pore diameter of 5.20, 4.80 and 3.46) was studied. ZSM-5 with different silica to alumina ratios treated with NaOH/CTAB ratio 0.18 (ZSM-5-80 (0.18), ZSM-5-280 (0.18), and ZSM-5-1500 (0.18) with pore diameter of 3.52, 3.02, and 2.50) and ZSM-5-80 (0.62), ZSM-5-280 (0.62), and ZSM-5-1500 (0.62)) was studied with pore diameter of 3.91, 4.75, and 3.28, respectively. ZSM-5-80 (0.62) with functionalization of three different types of silanes designated as ZSM-5-80 (0.62)-S1, ZSM-5-80 (0.62)-S2, and ZSM-5-80 (0.62)-S3 was studied with pore diameters of 8.19 nm, 11.35 nm and 6.72 nm, respectively.

The structured silicas such as mesocellular foam designated as Si-MSU-Foam (16.4 nm), aluminum containing mesocellular foam, Al-MSU-Foam (18.5 nm), Spherical micron sized silica (19 nm), Silicalite (2.68 nm), SiSBA-16 (3.3 nm), ULPFDU-12 (4.7 nm), SiKIT-6 (5.7 nm), SiMSU-Foam (16.4 nm), AlMSU-Foam (18.5 nm) and Q10 silica (19 nm) was also studied for CoQ10 adsorption, respectively. Steamed parent ZSM-5-80 sample with pore diameter of 3.1 nm and steamed hierarchical ZSM-5-80 (0.62) with pore diameter of 2.84 nm was also studied (FIG. 9).

These data show that in case of tested hierarchical aluminosilicates and structured mesosilicas, the adsorption remains between the percentage ranges of 18-55%, while ZSM-5-80 (0.62) with pore size of 3.91 nm showed highest adsorption of 55%. Interestingly, CoQ10 with molecular size of 5.6 nm, the pore sizes between 3-4 nm showed highest adsorption, while larger pore sizes favors comparatively less CoQ10 adsorption. The micron sized spherical silica with pore diameter of 19 nm showed 53.3% adsorption, followed by siliceous form of hexagonal MCM-41 (3.1 nm) with 51%, respectively. AlMSU-foam (18.5 nm) and siliceous MSU-foam (16.4 nm) showed Q10 adsorption of 49.9% and 46.7%, respectively. CoQ10 adsorption over siliceous supports such as cubic shaped three-dimensional SiKIT-6 showed 46.6%, followed by mesostructured ULPFDU-12 (45.7%), cubic shaped SBA-16 (44.5%), and Silicalite (44.1) in ranked order.

Selected nanosupports such as ZSM-5-80 (0.62), AlMSU-Foam, SiMSU-Foam, SiMCM-41, SiSBA-16, ULPFDU-12, micron sized spherical silica, SiKIT-6 were evaluated for curcumin adsorption (1500 ppm solution prepared using 10% methanol-PBS mixture). In case of curcumin, the adsorption on all the nanocarriers was higher than 80%, except silicalite which showed 75%. Specifically, hierarchical ZSM-5-80 (0.62), SiSBA-16 and AlMSU-F showed the highest adsorption of about 98% among different supports, followed by hexagonal SiMCM-41 (96.3%), ULPFDU-12 (95.6%), SiMSU-F (95.7%), SiKIT-6 (94.5%), and silicalite (75%), respectively.

In case of adsorption of ascorbic acid at concentration of 100 ppm, among the different structured materials, hexagonal MCM-41 had the highest adsorption (94.6%), followed closely by cubic shaped mesostructure ULPFDU-12 (91%), micronsized spherical silica (88%), AlMSU-F (84.0%), SiKIT-6 (80.7%) and SiSBA-16 (80.4%) in ranked order. Silicalite with micropores exhibited a significantly reduced adsorption (45.1%) in comparison to the previously mentioned supports, followed by cellular foam type silica SiMSU-F (41%) and ZSM-5-80 (0.62), which showed highest adsorption over CoQ10 and curcumin showed the lowest adsorption of 19.6%. On the other hand, AlMSU-F, the aluminum inserted silica foam showed highest ascorbic adsorption than SiMSU-F. For example, ascorbic acid adsorption over SiMSU-F was about 40.98%, which significantly increased to 84.02% over aluminum containing cellular foam indicating over 100% increase than siliceous foam.

Figure 11:
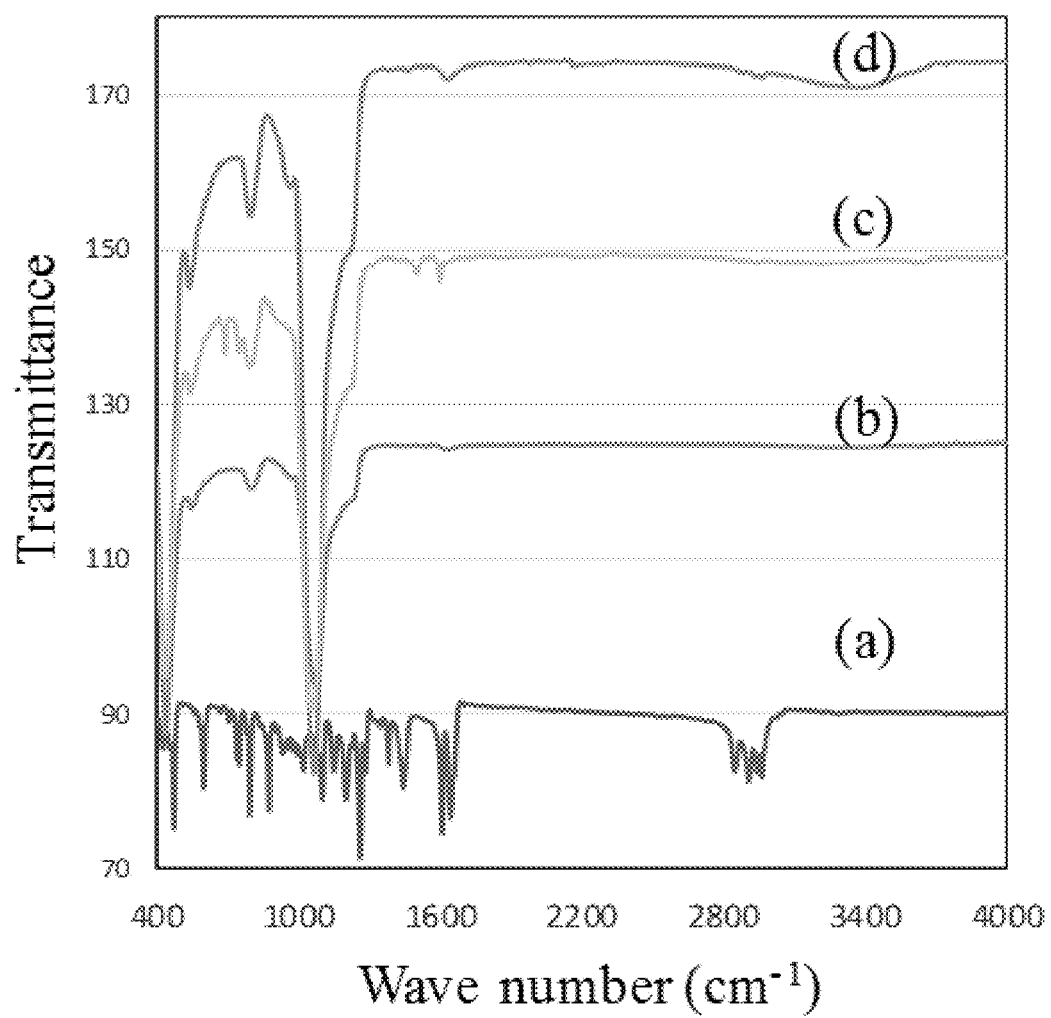
FIG. 11. FTIR spectroscopy of (a) CoQ10, (b) CoQ10-ZSM-5-80 (0.62), (c) CoQ10-ZSM-5-80 (0.62)-S1, and (d) CoQ10-ZSM-5-80 (0.62)-S2, respectively.

Unlike some other antioxidants such as resveratrol which is a natural polyphenol (3,5,4' trihydroxy trans stilbene) that is poorly soluble in water (50 microgram per ml), Coenzyme Q10 is built with a quinone-based structure containing 10 isoprene units and is extremely insoluble in water (<0.7 ng/ml). The inventors have recognized that poor bioavailability of an antioxidant correlates with a highly crystalline and hydrophobic structure, while particle size reductions has been found to increase bioavailability. Compared to silicas like SBA-16 or MCM-41, hierarchical nanocarriers according to the invention have unique textural characteristics such as high mesopore surface area and weak acidity that helps to coordinate with insoluble antioxidants like CoQ10 and convert them from a crystalline form to an amorphous nano-form. The XRD and FTIR results in indicate the complete transformation of crystalline form of CoQ10 into an amorphous form characterized by disappearance of crystalline peaks of CoQ10 (FIGS. 10 and 11). This shows the effective coordination influence of hierarchical pores of the nanocarriers according to the invention. The presence of protons at the external site tends to coordinate with quionone structure, while the Lewis acid site coordinates to electron rich isoprene units.

Figure 16:
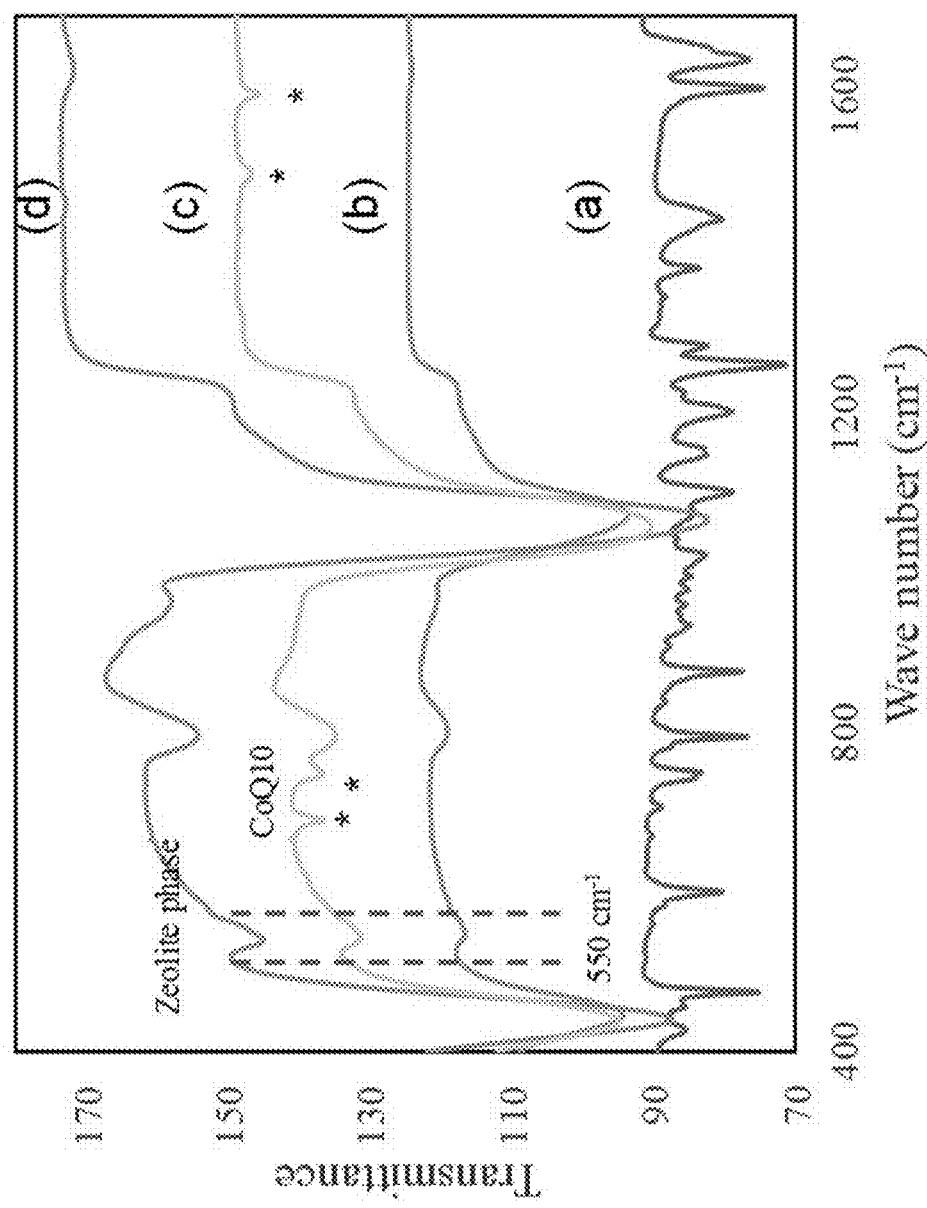
FIG. 16 shows the FTIR spectra of (a) CoQ10, (b) ZSM-5-80 (0.62), (c) CoQ10-ZSM-5-80 (0.62)-S1, and (d) CoQ10-ZM-5-80 (0.62), respectively.

Additional characteristics of the invention are depicted by FIGS. 15-17.

FIGS. 15A-15D, respectively, show the XRD diffraction spectra of CoQ10, ZSM-5-80 (0.62), ZSM-5-80 (0.62)-S1 and ZSM-5-80 (0.62)-S2.

FIG. 16 shows the FTIR spectroscopy of (a) CoQ10, (b) ZSM-5-80 (0.62), (c) CoQ10-ZSM-5-80 (0.62)-S1, and (d) CoQ10-ZSM-5-80 (0.62).

Figure 17A:
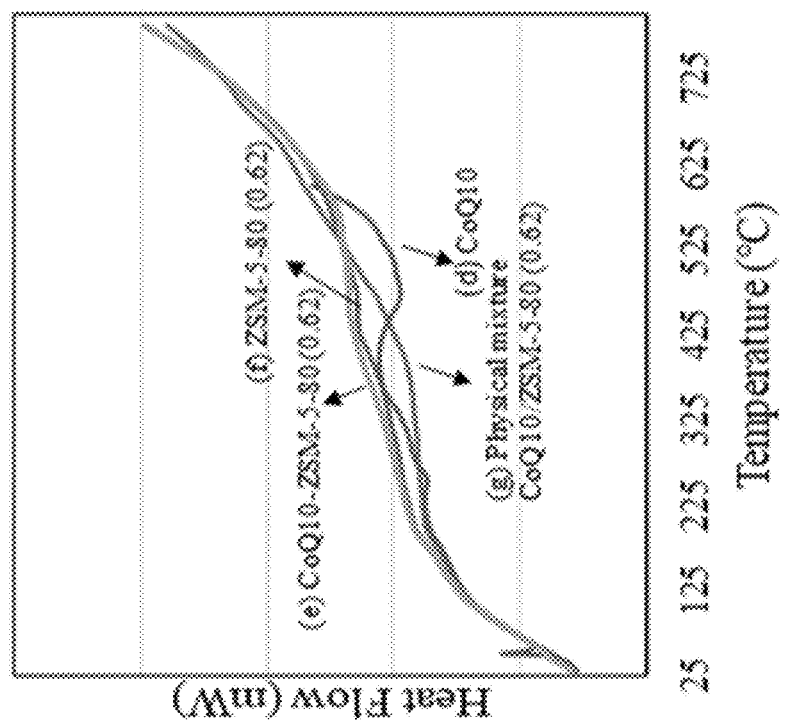
FIG. 17A shows the thermogravimetric analysis of (a) calcined ZSM-5-80 (0.62), (b) CoQ10-ZSM-5-80 (0.62), and (c) CoQ10, respectively.

FIG. 17A at (a-c) shows the thermogravimetric analysis of (a) calcined ZSM-5-80 (0.62), (b) CoQ10-ZSM-5-80 (0.62), and (c) CoQ10, respectively. The TGA thermogram of calcined ZSM-5-80 (0.62) shows no significant decomposition profile at the studied temperature range, while CoQ10 shows a clear decomposition pattern between 230-450° with no solid residues. In case of CoQ10-ZSM-5-80 (0.62), an intermediate decomposition profile different than ZSM-5-80 (0.62) and CoQ10 appears, indicating a difference in the thermal degradation behavior of such nanoformulation.

Figure 17B:
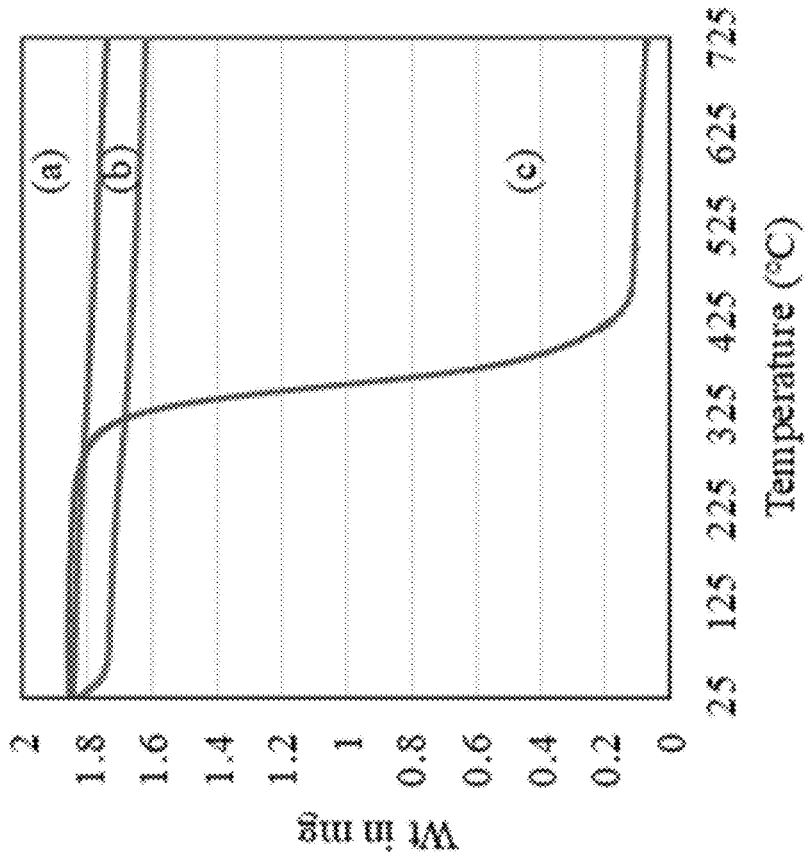
FIG. 17B shows the DSC profiles of (d) CoQ10, (e) CoQ10-ZSM-5-80 (0.62), (f) ZSM-5-80 (0.62) and (g) physical mixture of CoQ10/ZSM-5-80 (0.62).

FIG. 17B (d)-(g) show the DSC profiles which are sensitive to crystalline phase of adsorbed antioxidant. The DSC curve of CoQ10 showed two types of endotherms between 195-360° and 400-600° (d). In case of CoQ10-ZSM-5-80 (0.62), no such characteristic endothermic peaks was observed and remains similar to that ZSM-5-80 (0.62) (e) and (f). On the other hand, physical mixture of CoQ10 and ZSM-5-80 (0.62), showed similar endothermic peaks to that of crystalline CoQ10 (g). The study shows the complete transformation of crystalline CoQ10 into an amorphous structural form in combination with ZSM-5-80 (0.62).

As shown in the Examples, meso aluminosilicate composites having selected structures provide for effective adsorption of hydrophobic antioxidants like CoQ10 and curcumin. The inventors have demonstrated that through top down methodology, full grown zeolitic crystal can be broken down by alkali treatment into nanozeolitic subunits, however the hierarchical micro and mesophase reassembly in presence of cationic surfactant cetyltrimethyl ammonium bromide depends on the crystal size and silica to alumina ratios (FIG. 1). The hydrothermal stability study through steaming shows that hierarchical ZSM-5 with higher silica to alumina ratios such as 80, 280 and 1500 showed high steam stability than ZSM-5 with silica to alumina ratio of 22, 23 and 27, respectively (FIG. 2). Textural surface area of hierarchical ZSM-5 by nitrogen adsorption isotherm (FIG. 3) shows that based on alkaline treatment ratio (NaOH/CTAB ratio of 0.18) through top-down approach induces defective holes leading to the bimodal pore sizes that varies depending on the ZSM-5 crystal sizes. Micron sized ZSM-5-27 showed the presence of dual type of pores centered at 2.32 nm and 3.89 nm, ZSM-5-22 with crystal size of 2 μm showed pore size at 2.84 nm, while nano sized ZSM-5 showed unimodal pores centered at 3.89 nm. In case of silica to alumina ratio 80, 280 and 1500, hierarchical ZSM-5 with high mesoporous characteristics was observed. The ammonia TPD study shows the presence of ammonia adsorption on weak, medium and strong acid sites with variable degree of total acidity over conventional ZSM-5 and hierarchical ZSM-5 (FIG. 4). The morphological study using SEM and TEM analysis showed the ZSM-5 of variable sizes with similar silica to alumina ratio and pore ordering difference including ZSM-5 and MCM-41 interlinkage (FIG. 5). Moreover, from Table 1, it can be seen that the textural characteristics are almost similar, while acidity variation was significantly observed with different crystal size of ZSM-5 (Table 3). Both the surface area and total pore volume of ZSM-5-80 (0.62) sample was found to be higher, thereby increases the adsorption capacity (FIGS. 6 and 7). The study shows that tuning property of external surface area and pore volume was beneficial for adsorption of long chain hydrophobic CoQ10 molecules. Clearly combined investigation of adsorption activity with respect to FIGS. 6-8 show synergistic action for adsorption of CoQ10.

In order to evaluate the physical nature of CoQ10-nanosupport adsorption, the samples were analyzed using XRD and FT-IR (FIGS. 15A-15D and FIG. 16). In case of ZSM-5-80 (0.62), a complete transformation of crystalline CoQ10 to amorphous form was observed, indicating the importance of textural characteristics in terms of external surface area in a well-designed hierarchical character of ZSM-5-80 (0.62). However, over silane functionalized ZSM-5-80 (ZSM-5-80 (0.62)-S1, and ZSM-5-80 (0.62)-S2), an incomplete transformation of crystalline Q10 to amorphous form clearly shows the role of external surface area and pore volume which are blocked due to functionalization. The effect of structural confinement of various antioxidants stabilizing through hydrogen/electrostatic interactions was found to depend on textural features of hierarchical ZSM-5, where adsorption behavior shows the necessity of synergistic participation of hierarchical external surface area, pore volume, and weak acidity to solvate and stabilize the adsorption. Comparatively, hierarchical ZSM-5-80 (0.62) exhibited highest adsorption behavior than many of available mesoporous silicas and medium pore zeolites (FIG. 9). In case of ZSM-5-80 (0.62) sample, acid-base type interactions are predicted to be dominant, while in the case of steamed sample, the $Al^{3+}$ cations are proposed to be present at the more exposed position leading to a weaker link in the framework. In case of foam type of nanosupport, the presence of accessible aluminum containing foam type of structure shows considerable positive effect in ascorbic acid adsorption.

FIG. 17A at (a-c) shows the thermogravimetric analysis of (a) calcined ZSM-5-80 (0.62), (b) CoQ10-ZSM-5-80 (0.62), and (c) CoQ10, respectively. The TGA thermogram of calcined ZSM-5-80 (0.62) shows no significant decomposition profile at the studied temperature range, while CoQ10 shows a clear decomposition pattern between 230-450° with no solid residues. In case of CoQ10-ZSM-5-80 (0.62), an intermediate decomposition profile different than ZSM-5-80 (0.62) and CoQ10 appears, indicating a difference in the thermal degradation behavior of such nanoformulation.

FIG. 17B (d)-(g) show the DSC profiles which are sensitive to crystalline phase of adsorbed antioxidant. The DSC curve of CoQ10 showed two types of endotherms between 195-360° and 400-600° (d). In case of CoQ10-ZSM-5-80 (0.62), no such characteristic endothermic peaks was observed and remains similar to that ZSM-5-80 (0.62) (e) and (f). On the other hand, physical mixture of CoQ10 and ZSM-5-80 (0.62), showed similar endothermic peaks to that of crystalline CoQ10 (g). The study shows the complete transformation of crystalline CoQ10 into an amorphous structural form in combination with ZSM-5-80 (0.62).

While not being bound to any particular theory or explanation, based on these data, the favorable adsorption of CoQ10 over ZSM-5-80 (0.62) is proposed to occur through hydrogen bonding/electrostatic attraction (FIG. 14, Scheme 2). However, the presence of aluminum in the hierarchical mesozeolitic framework is proposed to generate Lewis acid sites with top-down methodology (FIG. 7) and tends to coordinate with electron rich isoprene units the through electrostatic attraction. The isomorphous substitution of silicon by aluminum atom induces negative charge that is stabilized by $H^+$. While not being bound to any particular theory or explanation, the inventors believe that the adsorption of CoQ10 may occur due to a synergistic coordination between and quionone which depends on the physicochemical characteristics of the structural framework of a hierarchical zeolite.

These data also show an adsorption pattern where an amount of Q10 adsorption was found to be independent on the hierarchical pore sizes but rather on the external surface area, pore volume and weak acid sites that eventually coordinate with electron rich Q10 through hydrogen bonding and electrostatic attraction rather than mere physical adsorption process. In case of ZSM-5-80 (0.62) sample, acid-base type interactions are predicted to be dominant. In particular, coordination of carbonyl group of quinone to the protonic site of zeolite, and electron rich double bond of isoprene unit to extra framework $Al^{3+}$ cation are proposed coordination site at the accessible external surface area of hierarchical ZSM-5-80 (0.62). In case of steamed sample, the reduced CoQ10 adsorption can be attributed to the $Al^{3+}$ cations at more exposed position inducing weaker link to the framework for possible synergistic action.

As shown herein, the inventors have produced hierarchical aluminosilicate nanocarriers that provide a superior capacity to adsorb antioxidants, such as long chain hydrophobic antioxidant CoQ10, curcumin, and hydrophilic ascorbic acid. These nanocarriers are produced by selection of a combination parameters including high surface area, pore volume and silica to alumina ratio.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A composition comprising:
   curcumin, and
   a hierarchical aluminosilicate having
   an $SiO_2/Al_2O_3$ ratio ranging from 22 to 80, and
   an external surface area of 295 to 785 $m^2/g$,
   a mesopore volume of from 0.11 to 0.78 cc/g, and
   a bimodal mesopore diameter distribution with a first pore diameter at 2.3 nm and a second pore diameter at 3.8 nm:
   wherein the curcumin is adsorbed onto the hierarchical aluminosilicate in an amorphous form,
   wherein the hierarchical aluminosilicate has a curcumin adsorption of about 98%, and
   wherein said composition comprises at least 30 wt % of the curcumin based on the total weight of the composition.

2. The composition of claim 1, wherein the hierarchical aluminosilicate has a pore volume ranging from 0.5 to 0.8 cc/g.

3. The composition of claim 1, wherein the hierarchical aluminosilicate has a stable zeolitic framework that retains at least 95% of its presteaming external surface area after water steaming at 700-750° C. for 2 hours.

4. The composition of claim 1, wherein the hierarchical aluminosilicate has a weak acidity ranging from 0.025 to 0.04 mmol/g and a total acidity that does not exceed 0.12 mmol/g and/or comprises weak acid sites, wherein the weak acid sites represent from 15-75% of the total acid sites.

5. The composition of claim 1, wherein the hierarchical aluminosilicate is produced by a top-down methodology comprising treating ZSM-5 with NaOH/CTAB at a ratio between 0.1 to 1.0, neutralizing the treated ZSM-5, drying the neutralized ZSM-5, and calcining the dried ZSM-5 product at a temperature of 500° C. to 800° C.

6. The composition of claim 1 that further comprises chitosan, polyacrylic acid, PLGA, or another biocompatible agent.

7. The composition of claim 1 that further comprises super paramagnetic iron oxide nanoparticles, SPIONs.

8. The composition of claim 1, wherein the hierarchical aluminosilicate is in the form of microcrystals having a crystal sizes of from 0.5 to 3 μm.

* * * * *